(12) United States Patent
Ramirez et al.

(10) Patent No.: US 8,674,103 B2
(45) Date of Patent: Mar. 18, 2014

(54) LYOTROPIC LIQUID CRYSTAL SYSTEMS BASED ON AROMATIC TETRACARBOXYLIC BISBENZOIMIDAZOLE DERIVATIVES AND METHODS FOR MAKING

(75) Inventors: Robert Ramirez, Mission Viejo, CA (US); Shijun Zheng, San Diego, CA (US); Zongcheng Jiang, Oceanside, CA (US); Shuangxi Wang, Corona, CA (US); Michiharu Yamamoto, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 237 days.

(21) Appl. No.: 13/203,412

(22) PCT Filed: Feb. 24, 2010

(86) PCT No.: PCT/US2010/025264
§ 371 (c)(1),
(2), (4) Date: Aug. 25, 2011

(87) PCT Pub. No.: WO2010/099223
PCT Pub. Date: Sep. 2, 2010

(65) Prior Publication Data
US 2011/0317102 A1    Dec. 29, 2011

Related U.S. Application Data

(60) Provisional application No. 61/155,970, filed on Feb. 27, 2009, provisional application No. 61/229,470, filed on Jul. 29, 2009.

(51) Int. Cl.
| | | |
|---|---|---|
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |

(52) U.S. Cl.
USPC .......................................... 546/27; 349/117

(58) Field of Classification Search
USPC .......................................... 349/117; 546/72
See application file for complete search history.

(56) References Cited

U.S. PATENT DOCUMENTS

| | | |
|---|---|---|
| 5,739,296 A | 4/1998 | Gvon et al. |
| 6,174,394 B1 | 1/2001 | Gvon et al. |
| 7,015,990 B2 | 3/2006 | Yeh et al. |

FOREIGN PATENT DOCUMENTS

| | | |
|---|---|---|
| CN | 1 777 604 | 5/2006 |
| DE | 456 236 | 2/1928 |
| EP | 0 081 143 | 6/1983 |
| EP | 0 143 979 | 6/1985 |
| EP | 0 785 477 | 7/1997 |
| EP | 0 961 138 | 12/1999 |
| EP | 1 795 532 | 6/2007 |
| WO | WO 02/063660 | 8/2002 |
| WO | WO 2004/096805 | 11/2004 |
| WO | WO 2005/089094 | 9/2005 |
| WO | WO 2007/030934 | 3/2007 |
| WO | WO 2008/020213 | 2/2008 |
| WO | WO 2010/099223 | 9/2010 |

OTHER PUBLICATIONS

Arient et al., Imadzol-Farbstoffe XV. Darstellung von Aroylenimidazolfarbstoffen und Einfluss der Substitution auf ihre Farbigkeit, Collection Czechoslovak Chemical Communications, 1965, vol. 30, pp. 3718-3729.
Bahadur, Birenda, Liquid Crystals Applications and Uses, World Scientific, Singapore—N.Y., 1990, vol. 1, p. 101.
Bobrov et al., "Environmental and Optical Testing of Optiva Thin Crystal Film™ Polarizers," Revised Version of the Proceedings of the 10th SID Symposium (ADT '01) Minsk, Republic of Belarus, Sep. 18-21, 2001, pp. 23 to 30.
Lukáč et al., "Darstellung und Fluoreszenzverhalten von 2,3,4,4a,10a,11,12,13-Octahydro-1,4a,10a,14-tetraazaviolanthron-Derivaten," Berichte der deutschen chemischen Gesellschaft, 1983, vol. 116, pp. 3524-3528.
Lydon, John, "Chapter XVIII Chromonics," Handbook of Liquid Crystals, 1998, pp. 98-1007.
International Search Report and Written Opinion in PCT Application No. PCT/US2010/025264 dated Jun. 4, 2010.

*Primary Examiner* — Phu Vu
(74) *Attorney, Agent, or Firm* — Knobbe, Martens, Olson & Bear LLP

(57) ABSTRACT

Compounds derived from aromatic tetracarboxyl bisbenzoimidazoles are disclosed. These compounds are capable of forming liquid crystal systems that can produce optically isotropic or anisotropic films with desirable optical properties. Formulae (I) or (II), or a salt thereof; wherein y is an integer in the range from 0 to about 4.

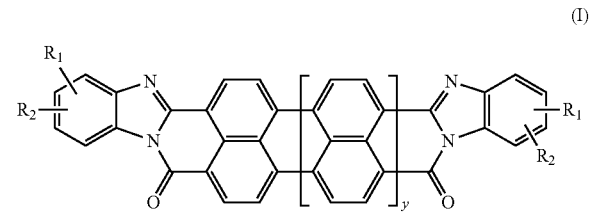

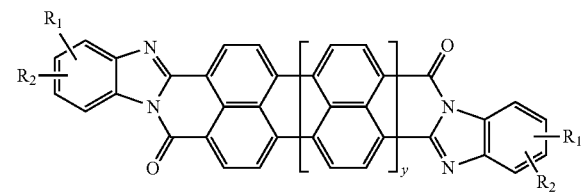

37 Claims, No Drawings

LYOTROPIC LIQUID CRYSTAL SYSTEMS BASED ON AROMATIC TETRACARBOXYLIC BISBENZOIMIDAZOLE DERIVATIVES AND METHODS FOR MAKING

CROSS-REFERENCE TO RELATED APPLICATIONS

This application claims priority to U.S. Provisional Patent Application No. 61/155,970, which was filed on Feb. 27, 2009, and U.S. Provisional Patent Application No. 61/229,470, which was filed on Jul. 29, 2009, both of which are incorporated by reference in their entirety.

BACKGROUND OF THE INVENTION

1. Field of the Invention

The present invention relates generally to the fields of organic chemistry and optically anisotropic coatings. More specifically, the present invention relates to lyotropic chromophoric compounds, lyotropic liquid crystal systems comprising one or more lyotropic chromophoric compounds, and optically isotropic or anisotropic films.

2. Description of the Related Art

Optical elements are increasingly based on new materials possessing specific, precisely controllable properties. An important element in many modern visual display systems is an optically anisotropic film having a combination of optical and other characteristics that can be adjusted to suit the requirements of a particular device, since each device often has its own set of requirements.

The increased popularity of liquid crystal displays (LCDs) has motivated studies of various liquid crystal (LC) compounds. Earlier researchers focused on thermotropic LC compounds that could be oriented into anisotropic films by mechanical forces. However, the forced orientation of the molecules in a thermotropic LC film would tend to disappear when the forces were discontinued. On the other hand, lyotropic liquid crystal (LLC) films are capable of retaining their dichroic orientation after the mechanical force is removed. Suitable materials include those that are capable of forming LC mesophases that can be oriented to form an anisotropic film.

Various polymeric materials have been used in the manufacture of optically anisotropic films. Films based on such materials may acquire anisotropic optical properties through uniaxial extension and modification with organic dyes or iodine. In many applications, the base polymer is polyvinyl alcohol (PVA). Such films are described in greater detail in the monograph Liquid Crystals: Applications and Uses, B. Bahadur (ed.), World Scientific, Singapore—N.Y. (1990), Vol. 1, p. 101. However, the low thermal stability of PVA-based films can limit their application. Development of new materials and methods for the synthesis of optically anisotropic films possessing improved characteristics is therefore quite advantageous. Particularly, films having properties such as higher heat resistance, convenient synthesis, and uniformity are highly desirable.

In recent years, there has been increasing demand for films possessing high optical anisotropy that are also characterized by improved selectivity in various wavelength ranges. Films having absorption maxima at different locations in the wide spectral range from the infrared (IR) to the ultraviolet (UV) are very desirable. Organic dichroic molecules are known to pack into supramolecular complexes that are generally shaped like columns. These columns form the basic structural units of a mesophase, and the mesophases can be oriented to form an anisotropic film with strong dichroism. Anisotropic materials have been synthesized based on water soluble organic dyes, for examples, in U.S. Pat. Nos. 5,739,296 and 6,174,394 and European patent EP 0961138. These materials exhibit high absorbance in the visible spectral region. While they may be advantageous for many applications, the absorbance profiles of these compounds limit their application in forming transparent double refraction films.

Additionally, currently available film application technologies typically require that the process parameters, for examples, dye concentration, film formation temperature, etc., be thoroughly selected and strictly followed during the formation of the films. However, even if all the conditions of film formation are precisely controlled, random local variation of the coating regime may still occur due to the formation of misorientation zones and/or microdefects. This may be a result of non-uniform micro- and macrocrystallization processes in the course of solvent removal upon applying the LLC system (e.g., LLC solution) onto a substrate surface. In addition, the probability of forming a coating with non-uniform thickness using the currently available dyes remains high, which in turn decreases the reproducibility of the target film parameters.

Anisotropic films that are selective in different wavelength ranges are required by growing number of new applications. It is therefore desirable to develop new varieties of compounds capable of forming an LLC phase and films with the required properties. Films with different absorbance maxima location in wide spectral range from the infrared to the ultraviolet are also desirable. However, only a small number of currently available dyes are useful in the formation of lyotropic mesophase. Thus, new LC dyes are now an object of attention.

Optically anisotropic films may be formed on glass, plastic, or other substrate materials. Films which exhibit high quality optical characteristics may be used as polarizers, which are described in Bobrov, et al., Environmental and Optical Testing of Optiva Thin Crystal Film® Polarizers, Proceedings of the 10th SID Symposium "Advanced display technologies," (Minsk, Republic of Belarus, Sep. 18-21, 2001), p. 23 to 30. Methods for the preparation of such films, including those with a high degree of crystallinity, are described in PCT Publication No. WO 02/063,660. The aforementioned PTCA derivatives are capable of forming LLC phases, and anisotropic films obtained using the LLC system possess excellent optical characteristics and exhibit good performance as polarizers.

Naphthalene- and perylene-tetracarboxyl bisbenzoimidazole disulfoderivatives are dichroic dyes capable of forming LLC systems that are also useful for the preparation of optical anisotropic films. Both naphthalene- and perylene-tetracarboxyl bisbenzoimidazole are insoluble in water, but may be converted to water-soluble form through a sulfonation process. To produce the disulfoderivative, an effective amount of naphthalene- or perylene-tetracarboxyl bisbenzoimidazole is added to oleum under prescribed conditions.

One of the main disadvantages of the previously described water-soluble naphthalene- and perylene-tetracarboxyl bisbenzoimidazole disulfoderivatives is the complexity of producing anisotropic films with uniform properties over the substrate surface. The complexity results from their phase instability, the likelihood of forming disorientation zones and micro- and macro-crystallization during solvent removal after the liquid crystal is coated on a substrate surface. These drawbacks complicated the process of forming films with high optical characteristics. Poor reproducibility necessitates accurate adjusting and strict control of fixed technological conditions at each film forming stage from coating to drying which may dramatically increase film production expense.

SUMMARY OF THE INVENTION

There is a general need for new and improved LLC systems based on aromatic tetracarboxylic bisbenzoimidazole derivatives. Described herein are a family of novel chemical compounds, including some tetracarboxylic bisbenzoimidazole compounds, capable of forming stable LLC mesophases and reliable transparent optical films.

An embodiment provides a lyotropic chromophoric compound represented by the general structural formulae (I) or (II), or a salt thereof:

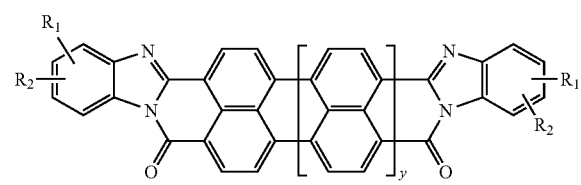

(I)

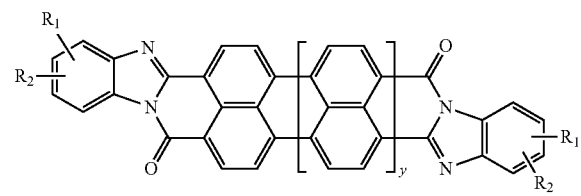

(II)

wherein y is an integer in the range from 0 to about 4 and each $R_1$ and $R_2$ is independently selected from the group consisting of —H, —OH, —NH$_2$, —Cl, —Br, —I, —NO$_2$, —F, —CF$_3$, —CN, —COOH, —CONH$_2$, optionally substituted C$_1$ to C$_6$ alkyl, optionally substituted C$_2$ to C$_6$ acetyl, optionally substituted C$_6$ to C$_{10}$ aryl, optionally substituted C$_2$ to C$_6$ alkynyl, optionally substituted C$_2$ to C$_6$ alkenyl, optionally substituted C$_1$ to C$_6$ alkoxyl, optionally substituted C$_1$ to C$_6$ alkylamino, -L$_1$-(M$_1$)$_r$, -L$_2$-(M$_2$)$_s$, and the following formulae (III), (IV), and (V):

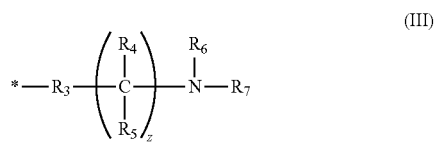

(III)

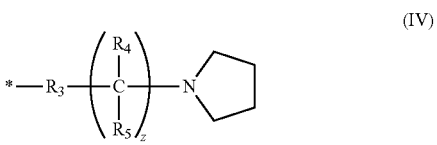

(IV)

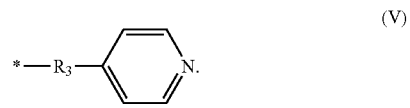

(V)

In an embodiment, L$_1$ and L$_2$ each independently represent a hydrophilic linker; each M$_1$ and M$_2$ independently represent an acidic group, a basic group, or a salt thereof; each r is independently 1 or 2; each s is independently 1 or 2; R$_3$ is independently selected from the group consisting of —NH—, —CONH—, —O— and —COO—; R$_4$, R$_5$, R$_6$, and R$_7$ are each independently selected from the group consisting of hydrogen, an optionally substituted C$_1$ to C$_6$ alkyl group, an optionally substituted C$_2$ to C$_6$ alkenyl group, an optionally substituted C$_2$ to C$_6$ alkynyl group, an optionally substituted C$_1$ to C$_6$ alkyl group substituted with at least one hydroxyl group, an optionally substituted C$_3$ to C$_8$ cycloalkyl group, an optionally substituted C$_6$ to C$_{10}$ aryl group, and an optionally substituted C$_7$ to C$_{16}$ aralkyl group; and, z is an integer in the range of 0 to about 4.

In an embodiment, the lyotropic chromophoric compound is represented by the general structural formulae (VI) or (VII):

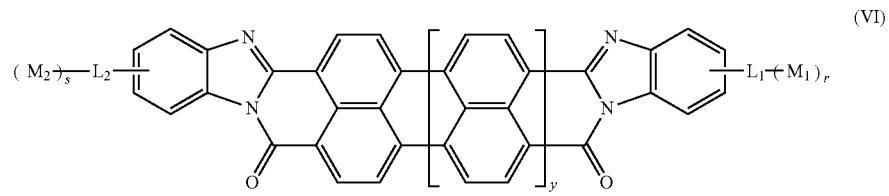

(VI)

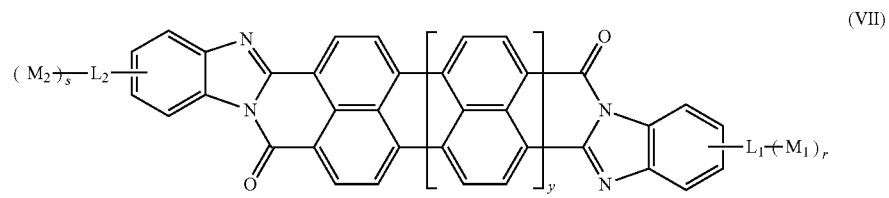

(VII)

wherein $L_1$ and $L_2$ each independently represent a hydrophilic linker; each $M_1$ and $M_2$ independently represent an acidic group, a basic group, or salt thereof; each r is independently 1 or 2; each s is independently 1 or 2; and y is an integer in the range from 0 to about 4.

In an embodiment, the lyotropic chromophoric compound is represented by the general structural formulae (XIV) or (XV), or a salt thereof:

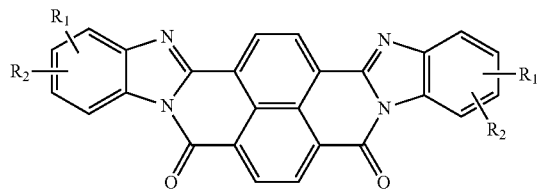

(XIV)

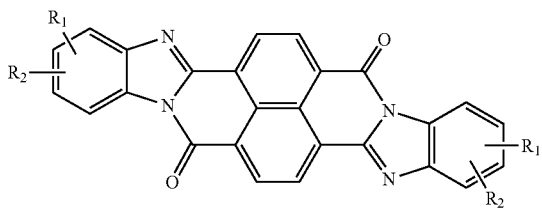

(XV)

wherein each $R_1$ and $R_2$ is independently selected from the group consisting of —H, —OH, —$NH_2$, —Cl, —Br, —I, —$NO_2$, —F, —$CF_3$, —CN, —COOH, —$CONH_2$, optionally substituted $C_1$ to $C_6$ alkyl, optionally substituted $C_2$ to $C_6$ acetyl, optionally substituted $C_6$ to $C_{10}$ aryl, optionally substituted $C_2$ to $C_6$ alkynyl, optionally substituted $C_2$ to $C_6$ alkenyl, optionally substituted $C_1$ to $C_6$ alkoxyl, optionally substituted $C_1$ to $C_6$ alkylamino, and any of the formulae (III), (IV), and (V), as set forth above.

The lyotropic chromophoric compounds described herein can be used in optical devices and systems used to manufacture such devices. An embodiment provides a lyotropic liquid crystal system comprising at least one lyotropic chromophoric compound as described above. In an embodiment, the lyotropic liquid crystal system comprises a solvent, such as water or water intermixed with an organic solvent. The compounds described herein can be used in the manufacture of anisotropic or isotropic optical films. Another embodiment provides an optically anisotropic film comprising at least one lyotropic chromophoric compound as described herein. The film can be formed by applying a lyotropic liquid crystal system described herein onto a substrate. The films described herein can be used in the manufacture of liquid crystal display devices.

In some embodiments, the lyotropic chromophoric compound represented by the general structural formula (I) is a compound having the general structural formula (VI). In some embodiments, the lyotropic chromophoric compound represented by the general structural formula (I) is a compound having the general structural formula (XIV). In some embodiments, the lyotropic chromophoric compound represented by the general structural formula (II) is a compound having the general structural formula (VII). In some embodiments, the lyotropic chromophoric compound represented by the general structural formula (II) is a compound having the general structural formula (XV). Thus, compounds of formulae (VI) and (XVI) are included in any discussion relating to formula (I), and compounds of formulae (VII) and (XV) are included in any discussion relating to formula (II).

These and other embodiments are described in greater detail below.

DETAILED DESCRIPTION OF THE INVENTION

Described herein are lyotropic chromophoric compounds that are capable of forming stable liquid crystals, and methods of synthesizing such compounds. The lyotropic chromophoric compounds described herein may generally be referred to as chromophores. Also provided are LLC systems, comprising a solvent and one or more lyotropic chromophoric compounds as described herein. Also provided are isotropic, anisotropic, or at least partially crystalline films based on these systems and compounds, and methods for manufacturing such films. Embodiments of the films described herein possess excellent optical properties and working characteristics.

Using dichroic dyes capable of forming LLC systems, it is possible to obtain films possessing a high degree of optical anisotropy. Optically anisotropic films may be formed on glass, plastic, or other substrate materials. Films having high dichroic ratios may be used as polarizers. Such films exhibit the properties of E-type polarizers, which are related to peculiarities of the optical absorption of supramolecular complexes, and behave as retarders (i.e., phase-shifting devices) in the spectral regions where the absorption is insignificant. The phase-retarding properties of these anisotropic films are related to their birefringence, that is, a difference in the refractive indices measured in the direction of application of the LLC system onto a substrate and in the perpendicular direction. A preferred LLC film formed from a strong (preferably light-fast) dye molecule-based LLC system is characterized by a high thermal stability and a good resistance to fading.

Embodiments described herein provide water soluble aromatic tetracarboxyl bisbenzoimidazole derivatives, and methods for preparing thin anisotropic films and optical elements based on these compounds. In an embodiment, the aromatic nature of the compounds are naphthalene-based or perylene-based. In an embodiment, the compounds described herein can be used to form stable LLC mesophases. Methods for manufacturing anisotropic and at least partially crystalline films based on these compounds are also provided. These films have highly desirable optical properties and working characteristics.

These and other advantages of the embodiments described herein can be achieved with a lyotropic chromophoric compound having the general structural formulae (I) or (II), as described above.

Each $R_1$ and $R_2$ in formulae (I) and (II) can be independently selected. $R_1$ and $R_2$ can be the same or different. Preferably, at least one of $R_1$ and $R_2$ is selected from the group consisting of -$L_1$-$(M_1)_r$, -$L_2$-$(M_2)_s$, and the formulae (III), (IV), and (V), as described above.

Each of the hydrophilic linking groups $L_1$ and $L_2$ in formulae (I), (II), (VI), and (VII) can be independently selected. $L_1$ and $L_2$ can be the same or different. A "hydrophilic linker" as described herein is a linking group with a length and composition that is effective to render the compound to which they are attached sufficiently soluble, such that the compound can react with a counter ion in a suitable solvent such as water. The hydrophilic linker need not, however, render the compound completely soluble in the chosen solvent before the counter ion is added. However, the hydrophilic linker should render the compound soluble in the solvent once a salt is formed with the counter ion. In an embodiment, the compound is at least partially soluble in water. In an embodiment, the compound is soluble in water. Preferably, $L_1$ and $L_2$ in formulae (I), (II), (VI), and (VII) are each independently selected from a linker having the general formula (VIII), which may or may not comprise a polyethyleneglycol group, a linker having the general formula (IX), which may or may not comprise a polypropyleneglycol group, and a linker having the general formula (X), which may or may not comprise a polyethyleneimine group:

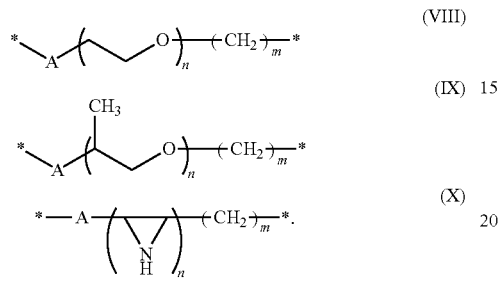

Each A in formulae (VIII), (IX), and (X) can independently represent a bond or, alternatively, is selected from the group consisting of:

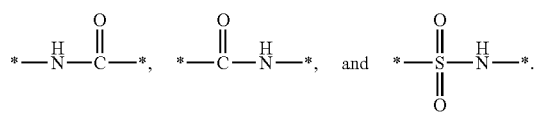

Each n in formulae (VIII), (IX), and (X) can be independently selected from an integer in the range of 0 to about 9. The hydrophilic nature of the linking group can be increased by using a larger number for n. In an embodiment, each n in formulae (VIII), (IX), and (X) can be independently selected from an integer in the range of about 1 to about 8. In an embodiment, each n in formulae (VIII), (IX), and (X) can be independently selected from an integer in the range of about 2 to about 7. In an embodiment, each n in formulae (VIII), (IX), and (X) can be independently selected from an integer in the range of 0 to about 3. In an embodiment, each n in formulae (VIII), (IX), and (X) can be independently selected from an integer in the range of about 3 to about 6. In an embodiment, each n in formulae (VIII), (IX), and (X) can be independently selected from an integer in the range of about 6 to about 9. Each m in formulae (VIII), (IX), and (X) can be independently selected from an integer in the range of 0 to about 6. The m in formulae (VIII), (IX), and (X) is selected to control the distance between the hydrophilic portion of the hydrophilic linker and the acidic group, basic group, or salt thereof. In an embodiment, m is selected to be an integer in the range of 0 to about 6. In an embodiment, m is selected to be an integer in the range of 1 to 3. In an embodiment, each m in formulae (VIII), (IX), and (X) can be independently selected from an integer in the range of 0 to about 2. In an embodiment, each m in formulae (VIII), (IX), and (X) can be independently selected from an integer in the range of about 2 to about 4. Preferably, at least one of n or m is at least 1.

The hydrophilic linker can be linear or branched. In an embodiment, $L_1$ and/or $L_2$ is independently selected from a linker that comprises the general formula (XI), a linker that comprises the general formula (XII) and a linker that comprises the general formula (XIII):

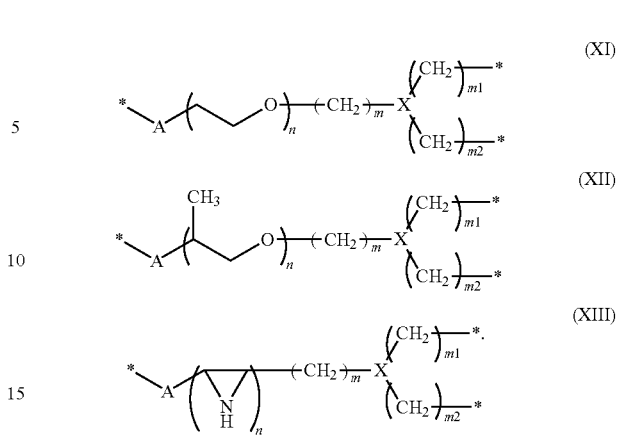

In an embodiment, each X in formulae (XI), (XII), and (XIII) independently represents N or P. In an embodiment, X is nitrogen. In an embodiment, when $L_1$ and/or $L_2$ comprise a linker having the general formulae (XI), (XII), or (XIII), then r in formulae (I), (II), (VI) or (VII) equals 2. In an embodiment, each A in formulae (XI), (XII), and (XIII) independently represents a bond or is selected from the group consisting of:

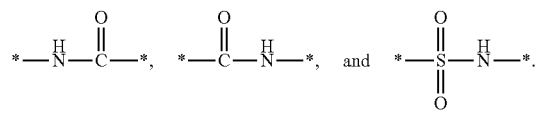

Each n in formulae (XI), (XII), and (XIII) can be independently selected from an integer in the range of 0 to about 9. In an embodiment, each n in formulae (XI), (XII), and (XIII) can be independently selected from an integer in the range of 1 to about 8. In an embodiment, each n in formulae (XI), (XII), and (XIII) can be independently selected from an integer in the range of 2 to about 7. In an embodiment, each n in formulae (XI), (XII), and (XIII) can be independently selected from an integer in the range of 0 to about 3. In an embodiment, each n in formulae (XI), (XII), and (XIII) can be independently selected from an integer in the range of about 3 to about 6. In an embodiment, each n in formulae (XI), (XII), and (XIII) can be independently selected from an integer in the range of about 6 to about 9. Each m, m1, and m2 in formulae (XI), (XII), and (XIII) can be independently selected from an integer in the range of 0 to about 6. In an embodiment, each m, m1, and m2 in formulae (XI), (XII), and (XIII) can be independently selected from an integer in the range of 0 to about 2. In an embodiment, each m, m1, and m2 in formulae (XI), (XII), and (XIII) can be independently selected from an integer in the range of about 2 to about 4. Preferably, at least one of n or m is at least 1.

Each $M_1$ and $M_2$ in formulae (I), (II), (VI), and (VII) can independently represent an acidic group, a basic group, or salt thereof. $M_1$ and $M_2$ can be the same or different. In embodiments where $M_1$ and/or $M_2$ of the chromophoric compound comprise an acidic group, the acidic group can be converted to a salt by intermixing the chromophoric compound with a suitable base. In embodiments where $M_1$ and/or $M_2$ of the chromophoric compound comprise a basic group, the basic group can be converted to a salt by intermixing the chromophoric compound with a suitable acid. Selection of the counter ion, e.g. formed from the reaction with the acid or base, can be determined by those having ordinary skill in the art, guided by the disclosure herein. Each $M_1$ and $M_2$ can be selected to be salts that configure the compound to be soluble in water or water intermixed with another organic solvent. For example, conversion of the acidic or basic groups into salts can increase the solubility of the compound. Thus solubility of the compound can be controlled by selection of the hydrophilic linker, e.g., the length of the hydrophilic portion of the hydrophilic linker and the salt group of $M_1$ and/or $M_2$.

In an embodiment, each $M_1$ and $M_2$ independently comprises an acidic group or basic group selected from —$CONH_2$, —COOH, —$SO_3H$, —SH, —$NR_8R_9$, —$PO(OH)_2$, —PO(OR')(OH), —$PO(OR')_2$, —OH, and the following structure:

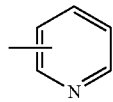

wherein R', $R_8$, and $R_9$ in the above structures are each independently selected from hydrogen, an optionally substituted $C_1$ to $C_6$ alkyl group, an optionally substituted $C_2$ to $C_6$ alkenyl group, an optionally substituted $C_2$ to $C_6$ alkynyl group, an optionally substituted $C_3$ to $C_8$ cycloalkyl group, an optionally substituted $C_6$ to $C_{10}$ aryl group, or an optionally substituted $C_7$ to $C_{16}$ aralkyl group.

In an embodiment, $M_1$ and $M_2$ are each independently selected to comprise an anion portion independently selected from —$PO_3^{2-}$, —PO(OR')$O^-$, —$SO_3^-$, and —$CO_2^-$, wherein R' is selected from hydrogen, an optionally substituted $C_1$ to $C_6$ alkyl group, an optionally substituted $C_2$ to $C_6$ alkenyl group, an optionally substituted $C_2$ to $C_6$ alkynyl group, an optionally substituted $C_3$ to $C_8$ cycloalkyl group, an optionally substituted $C_6$ to $C_{10}$ aryl group, or an optionally substituted $C_7$ to $C_{16}$ aralkyl group. The anion portion of $M_1$ and $M_2$ that is covalently attached the compound can be ionically bonded to one or more counter ions. In an embodiment, each $M_1$ and $M_2$ further comprises one or more counter ion. In an embodiment, the counter ion is independently selected from $H^+$, $NH_4^+$, $K^+$, $Li^+$, $Na^+$, $Cs^+$, $Ca^{++}$, $Sr^{++}$, $Mg^{++}$, $Ba^{++}$, $Co^{++}$, $Mn^{++}$, $Zn^{++}$, $Cu^{++}$, $Pb^{++}$, $Fe^{++}$, $Ni^{++}$, $Al^{3+}$, $Ce^{3+}$, $La^{3+}$, or a protonated organic amine, or similar counter ions. Examples of suitable protonated organic amines include $NH(Et)_3^+$, $NH_2(Et)_2^+$, $NH_3(Et)^+$, $NH(Me)_3^+$, $NH_2(Me)_2^+$, $NH_3(Me)^+$, $H_3NCH_2CH_2OH^+$, and $H_2NCH_2(CH_2OCH_2CH_2OH)^+$. In an embodiment, the counter ion is independently selected from $NH_4^+$ and $NH(Et)_3^+$. The number of counter ions can vary and may be fractional if the counter ion or ions are associated with more than one molecule. In an embodiment, one or more counter ions are shared by at least two molecules.

In an embodiment, $M_1$ and $M_2$ are each independently selected to comprise a cation portion independently selected from

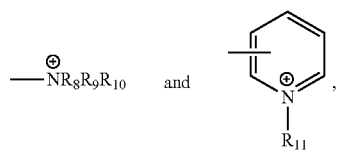

wherein $R_8$, $R_9$, $R_{10}$, and $R_{11}$ are each independently selected from hydrogen, an optionally substituted $C_1$ to $C_6$ alkyl group, an optionally substituted $C_2$ to $C_6$ alkenyl group, an optionally substituted $C_2$ to $C_6$ alkynyl group, an optionally substituted $C_3$ to $C_8$ cycloalkyl group, an optionally substituted $C_6$ to $C_{10}$ aryl group, or an optionally substituted $C_7$ to $C_{16}$ aralkyl group. In an embodiment, $R_8$, $R_9$, $R_{10}$, and $R_{11}$ are each independently selected from hydrogen, methyl, ethyl, n-propyl, isopropyl, n-butyl, isobutyl, sec-butyl, tert-butyl, and cyclohexyl. An appropriate counter ion can be selected. In an embodiment, the counter ion is independently selected from $CO_2CF_3^-$, $CH_3SO_3^-$, $Cl^-$, $Br^-$, and $I^-$. In an embodiment, the counter ion is $CH_3SO_3^-$. The number of counter ions can vary and may be fractional if the counter ion or ions belong to more than one molecule. In an embodiment, one or more counter ions are shared by at least two molecules.

In an embodiment, each y in formulae (I), (II), (VI), and (VII) is selected to be an integer in the range of 0 to 4. As y is increased, the aromatic nature of the compound is also increased. Increasing aromaticity can decrease the solubility of the compound. The peak at which absorbance occurs in the UV-Vis spectrum can be adjusted by increasing or decreasing y. Higher aromatic behavior generally causes peak absorption at higher wavelengths, whereas less aromaticity generally causes peak absorption at lower wavelengths. In an embodiment, y is selected to be an integer in the range of 0 to about 2.

In an embodiment, y is 0. Compounds represented by the general structural formulae (XIV) or (XV) are non-limiting embodiments in which y is 0. In an embodiment, each $R_1$ and $R_2$ in formulae (XIV) and (XV) can be independently selected. $R_1$ and $R_2$ can be the same or different. Each $R_1$ and $R_2$ is selected from the group consisting of —H, —OH, —$NH_2$, —Cl, —Br, —I, —$NO_2$, —F, —$CF_3$, —CN, —COOH, —$CONH_2$, optionally substituted $C_1$ to $C_6$ alkyl, optionally substituted $C_2$ to $C_6$ acetyl, optionally substituted $C_6$ to $C_{10}$ aryl, optionally substituted $C_2$ to $C_6$ alkynyl, optionally substituted $C_2$ to $C_6$ alkenyl, optionally substituted $C_1$ to $C_6$ alkoxyl, optionally substituted $C_1$ to $C_6$ alkylamino, and the following formulae (III), (IV), and (V):

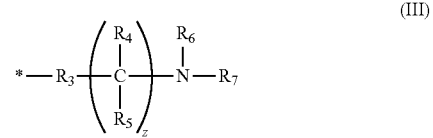

(III)

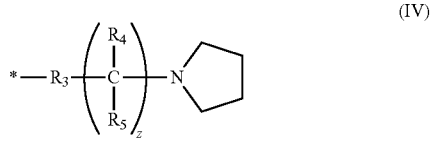

(IV)

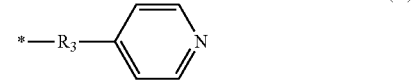

(V)

wherein $R_3$, $R_4$, $R_5$, $R_6$, $R_7$, and z are each as defined above. In embodiments where z is greater than 1, then $R_4$ and $R_5$ will both be present more than one time. Each $R_4$ and $R_5$ in embodiments where z is greater than 1 can be independently selected. In some specific embodiments, $R_4$, $R_5$, $R_6$, and $R_7$ are each independently selected from the group consisting of hydrogen, methyl, ethyl, n-propyl, isopropyl, n-butyl, isobutyl, sec-butyl, tert-butyl, hydroxymethyl, and cycloalkyl.

In an embodiment, salts of the lyotropic chromophoric compounds of general structural formulae (XIV) and (XV)

are provided. In an embodiment, the salts of compounds of general structural formulae (XIV) and (XV) are provided, wherein at least one of $R_1$ and $R_2$ comprises a nitrogen salt and a counter ion, $X^-$, wherein $X^-$ is selected from the group consisting of $F^-$, $Cl^-$, $Br^-$, $I^-$, $CH_3SO_3^-$, and $R_{12}COO^-$, wherein $R_{12}$ is selected from the group consisting of hydrogen, an optionally substituted $C_1$ to $C_4$ alkyl group, an optionally substituted $C_2$ to $C_4$ alkenyl group, an optionally substituted $C_2$ to $C_4$ alkynyl group, an optionally substituted $C_1$ to $C_4$ alkyl group substituted with at least one halogen, an optionally substituted $C_1$ to $C_4$ alkyl group substituted with at least one hydroxyl group, an optionally substituted $C_3$ to $C_8$ cycloalkyl group, an optionally substituted $C_6$ to $C_{10}$ aryl group, and an optionally substituted $C_7$ to $C_{16}$ aralkyl group. In an embodiment, a salt of a compound of general structural formulae (XIV) or (XV) is provided by protonation of an amine within the structural formulae (XIV) or (XV), e.g., in the substituent of formulae (III), (IV), or (V). In an embodiment, a salt of a compound of general structural formulae (XIV) or (XV) is provided by alkylation of an amine within the structural formulae (XIV) or (XV), e.g., in the substituent of formulae (III), (IV), or (V).

Conversion of the compound into a salt form can also be used to adjust the solubility of the compound. For example, the compound can be rendered partially water soluble or completely water soluble by alkylation of an amine within the structural formulae (XIV) or (XV). The solubility in water can further be controlled by selection of the appropriate counter ion.

Each of the alkyl, alkenyl, alkynyl, cycloalkyl, aryl, or aralkyl groups described herein as "optionally substituted" can be unsubstituted or substituted with one or more substituent group(s). When substituted, the substituent group(s) is (are) one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Non-limiting examples of the substituent group(s) include methyl, ethyl, propyl, butyl, pentyl, isopropyl, methoxide, ethoxide, propoxide, isopropoxide, butoxide, pentoxide and phenyl.

The alkyl, alkenyl, and alkynyl groups can be linear or branched groups. Some examples of alkyl groups include methyl, ethyl, n-propyl, isopropyl, n-butyl, isobutyl, sec-butyl, and tert-butyl. Additionally, the substituents can comprise a cycloalkyl group. For example, the cycloalkyl group can include cyclopentyl, cyclohexyl, or cyloheptyl. Some examples of useful aryl groups include phenyl, tolyl, naphthyl, phenanthryl, and anthracenyl. Some examples of useful aralkyl groups include benzyl, phenethyl, naphthylmethyl, phenanthylmethyl, and anthranylmethyl. Preferably, R', $R_1$, $R_2$, $R_4$, $R_5$, $R_6$, $R_7$, $R_8$, $R_9$, $R_{10}$, and $R_{11}$ are independently selected from hydrogen, methyl, ethyl, n-propyl, isopropyl, butyl, t-butyl, and cyclohexyl.

In some embodiments, compounds of the following general structural formula (XV)-A are provided:

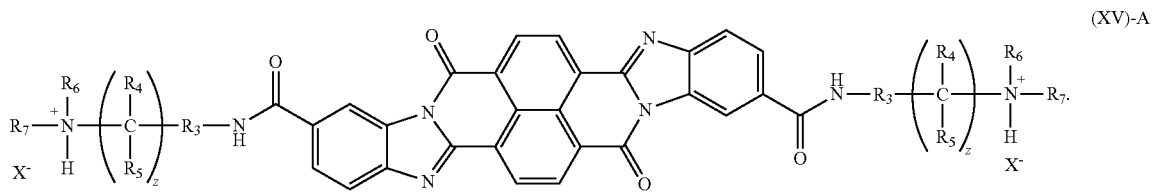

(XV)-A wherein z, $R_3$, $R_4$, $R_5$, $R_6$, and $R_7$ are as defined above, and the terminal amines of the compound are protonated. The associated counterion $X^-$ is independently selected from the group consisting of $F^-$, $Br^-$, $I^-$, $CH_3SO_3^-$, and $R_{12}COO^-$, wherein $R_{12}$ is independently selected from the group consisting of hydrogen, an optionally substituted $C_1$ to $C_4$ alkyl group, an optionally substituted $C_2$ to $C_4$ alkenyl group, an optionally substituted $C_2$ to $C_4$ alkynyl group, an optionally substituted halogen containing $C_1$ to $C_4$ alkyl group, an optionally substituted hydroxyl containing $C_1$ to $C_4$ alkyl group, an optionally substituted $C_3$ to $C_8$ cycloalkyl group, an optionally substituted $C_6$ to $C_{10}$ aryl group, and an optionally substituted $C_7$ to $C_{16}$ aralkyl group. In some embodiments, the terminal amines of the compound are alkylated to form ammonium salts with an associated counterion, $X^-$. The alkyl group that forms the ammonium salt is independently selected from the group consisting of methyl, ethyl, n-propyl, isopropyl, n-butyl, isobutyl, sec-butyl, and tert-butyl, and $X^-$ is independently selected from the group consisting of $F^-$, $Cl^-$, $Br^-$, $I^-$, $CH_3SO_3^-$, and $R_{12}COO^-$, wherein $R_{12}$ is independently selected from the group consisting of hydrogen, an optionally substituted $C_1$ to $C_4$ alkyl group, an optionally substituted $C_2$ to $C_4$ alkenyl group, an optionally substituted $C_2$ to $C_4$ alkynyl group, an optionally substituted halogen containing $C_1$ to $C_4$ alkyl group, an optionally substituted hydroxyl containing $C_1$ to $C_4$ alkyl group, an optionally substituted $C_3$ to $C_8$ cycloalkyl group, an optionally substituted $C_6$ to $C_{10}$ aryl group, and an optionally substituted $C_7$ to $C_{16}$ aralkyl group. Although the compounds of the general structural formula (XV)-A are trans compounds, the cis compounds can also be made by those having ordinary skill in the art, guided by the disclosure herein.

In some embodiments, compounds of formulae (XIV) or (XV) are provided wherein at least one of $R_1$ and $R_2$ is independently represented by the general formulae (III), (IV) or (V). In some embodiments, the compounds of formulae (XIV) or (XV) comprise an ammonium salt. In an embodiment, the compounds described herein are transparent in the wide visible spectrum range and are capable of forming LLC phases with increased stability over thermotropic liquid crystals. In an embodiment, the compound is transparent in the visible spectrum range of about 400 nm to about 700 nm. In an embodiment, the compound is transparent in the visible spectrum range of about 400 nm to about 600 nm. In an embodiment, the compound is transparent in the visible spectrum range of about 500 nm to about 700 nm.

The compounds described herein can be synthesized by one having ordinary skill in the art, guided by the disclosure herein, by way of commonly used techniques used to synthesize analogous lyotropic organic structures. One embodiment provides a procedure for synthesizing aromatic tetracarboxylbisbenzoimidazole carboxylamide derivatives. For example, controlled amounts of naphthalene- or perylenetetracarboxylic bisanhydride can be reacted with 3,4-diamino-benzoic carboxylamide for about 15 hours at a temperature range of about 120° C. to about 180° C. under argon using acetic acid or phenol as the solvent. The resulting product can be purified by ultrafiltration to produce the final water-soluble, naphthalene- and perylenetetracarboxylbisbenzoimidazole carboxylamide derivatives. In another embodiment, controlled amounts of 1,2-diaminobenzene or derivatives thereof are reacted with naphthalene- or perylenetetracarboxylic bisanhydride for about 15 hours at about 150° C. under argon using $Zn(OAc)_2$ and DMF as solvent. The resulting product is optionally either protonated or alkylated to produce a final water-soluble, tetracarboxylbisbenzoimidazole with a water-solubilizing group.

An "LLC system" as described herein is a solution comprising a solvent and one or more lyotropic chromophoric compounds as described herein. In an embodiment, the LLC system comprises an LLC mesophase. An LLC mesophase is formed when the concentration of lyotropic chromophoric compound in an LLC system is at or above the critical concentration for the formation of a liquid crystal within the system. The compounds described herein can be configured to absorb light in the visible spectrum range and also can be configured to form LLC systems with increased stability over thermotropic liquid crystals. These stable LLC systems may be used in the formation of anisotropic, isotropic, and/or at least partially crystalline films with highly reproducible, optimal optical characteristics. Film formation with greater uniformity and fewer microdefects upon solvent removal can be accomplished using embodiments of the LLC systems comprising the lyotropic chromophoric compounds described herein.

Embodiments of the LLC systems formed with the compounds described herein further possess increased stability over a broad range of concentrations, temperatures, and pH ranges. Thus, the systems and compounds simplify the process of anisotropic film formation and permit the use of a variety of techniques for creation of film layers. The production of films is facilitated with highly reproducible parameters, including dichroic ratio. Embodiments of the organic compounds described herein exhibit improved aqueous solubility. The increased optical anisotropy demonstrated by embodiments of the films comprising the chromophoric compounds is highly desirable. Without being bound by theory, the inventors believe that the high degree of optical anisotropy exhibited by certain embodiments is derived through non-covalent bonding, such as hydrogen bonding and cation-anion interactions, between two or more molecules.

The LLC systems can be formed over a broad range of pH. For example, the nitrogen-containing substituents according to formulae (III), (IV), and (V) can be protonated and formed into a salt, as discussed above. Also, the acidic, basic, or salt characteristic of $M_1$ and $M_2$ can be adjusted by one of ordinary skill in the art to affect the solubility in various pH solutions. In an embodiment, $M_1$ and/or $M_2$ comprises an acidic group, which the compound has a pH ranging from about 1 to about 6 in solution, depending on the concentration of the compound. In an embodiment, $M_1$ and/or $M_2$ comprises a basic group, which the compound has a pH ranging from about 8 to about 12 in solution, depending on the concentration of the compound.

Conversion of the acidic or basic groups into their salt forms can also be used to adjust the solubility of the compound. For example, solubility in water can further be controlled by selection of the appropriate counter ion. Additionally, certain counter ions, such as $Li^+$ among others, can improve the dichroic ratio of the compound.

The compounds having the general structural formulae (I) or (II) can form stable LLC systems both individually and in mixtures. Various combinations of compounds of formulae (I) and (II) can be used in the manufacture of LLC systems and films. In an embodiment, LLC systems described herein comprise at least one compound of formula (I) or (II), wherein at least one of $R_1$ and $R_2$ in the general formulae (I) or (II) is represented by the general formulae (III), (IV) or (V). In an embodiment, a LLC system comprises two or more compounds, wherein at least one compound has at least one of $R_1$ and $R_2$ represented by the general formula (III), and at least one compound has at least one of $R_1$ and $R_2$ represented by the general formula (IV). In an embodiment, a LLC system comprises two or more compounds that share a common general structure, $R_1$, and $R_2$, but differ in that at least one of $R_3$ to $R_7$ is different. In an embodiment, a LLC system comprises a first compound represented by the general formula (I) or (II), wherein at least one of $R_1$ and $R_2$ in the general formula (I) or (II) are each independently represented by the general formula (III), wherein the first compound has a concentration in the range of about 5% to about 50% by weight of the lyotropic liquid crystal system; a second compound represented by the general formula (I) or (II), wherein at least one of $R_1$ and $R_2$ in the general formula (I) or (II) are each independently represented by the general formula (IV), wherein the second compound has a concentration in the range of about 5% to about 50% by weight of the lyotropic liquid crystal system; and a third compound represented by the general formula (I) or (II), wherein at least one of $R_1$ and $R_2$ in the general formula (I) or (II) are each independently represented by the general formula (V), wherein the third compound has a concentration in the range of about 5% to about 50% by weight of the lyotropic liquid crystal system. In an embodiment, a LLC system disclosed herein comprises at least one compound represented by the general formula (XV)-A.

Furthermore, each of these compounds can be mixed with other known lyotropic compounds. In an embodiment, the compounds having the general structural formulae (I) and/or (II) are combined with other dichroic dyes capable of forming LLC phases to form LLC systems. In an embodiment, the compounds having the general structural formulae (I) and/or (II) are combined with other substances that are generally non-absorbing (colorless) or weakly absorbing in the visible range and capable of forming LLC systems. The LLC systems can be formed, for example, by intermixing the compounds with a solvent, such as water. After removal of the solvent, this LLC system can form an anisotropic, isotropic and/or at least partially crystalline film with reproducibly high optical characteristics. Methods and systems for forming stable LLC systems and resultant anisotropic, isotropic and/or at least partially crystalline optical films are described in greater detail in U.S. Pat. No. 6,563,640, the disclosure of which is incorporated by reference, particularly for the purpose of describing optical films and methods for making them.

Lyotropic chromophoric compounds in aqueous solutions as described herein typically exhibit a maximum optical absorption in the wavelength interval between about 400 nm to about 780 nm. In an embodiment, the chromophoric compounds in aqueous solutions exhibit a maximum optical absorption in the wavelength interval between about 450 nm to about 700 nm. The hydrophilic-hydrophobic balance of the molecular aggregates formed in LLC systems can be controlled when using the compounds described herein. For example, the chromophoric naphthalene or perylene core structure in formulae (I) and (II) (and also formulae (VI) and (VII)) can be adjusted by varying y (to produce tetra perylene or higher orders) to increase hydrophobicity. Furthermore, the length of the linkers having the general formulae (VIII), (IX), (X), (XI), (XII), or (XIII) can be increased to adjust hydrophilicity. By varying either or both of these parameters, one of ordinary skill can change the solubility of the compound and the solution viscosity when mixed with a solvent. Additionally, one of ordinary skill can also adjust the absorption wavelengths and produce chromophoric compounds that cover all or part of the full color wavelength spectrum.

Embodiments of the lyotropic chromophoric compounds described herein can be used to form stable lyotropic liquid crystal systems. LLC systems of individual compounds having the general structural formulae (I) or (II), as well as mixtures of such compounds, can be prepared by one of ordinary skill in the art, guided by the disclosure herein.

One or more of the compounds described herein can be intermixed with a solvent to form an LLC system, which can then be applied onto a substrate surface and oriented by any known method such as, for example, those described in PCT Publication Nos. WO 94/28073 and WO 00/25155, the disclosures of which are incorporated by reference. The types of substrate suitable for making optically anisotropic films may include transparent/translucent substrates, such as glass, plastic, color filter, and transparent/translucent polymer sheet, and semiconductors. In some embodiments, the LLC system is applied onto a substrate by means of spraying, pouring, printing, coating, dipping or transferring by a spoon, a spatula, a rod or any object capable of transferring a liquid crystal system. The desired orientation of the liquid crystals may be provided, for example, by applying shear stress, gravitational force, or an electromagnetic field. In some embodiments, an applicator rod or suitable tools may be used to apply pressure on the surface to orient or arrange the LLC system. A linear velocity in the range of about 25 mm/s to about 1 m/s can be applied on the film surface to orient the liquid crystal mesophases. The film forming process may be carried out at room temperature. In some embodiments, the relative humidity during orientation may be in the range of from about 55% to about 85%. In some embodiments, diimides described herein provide one of the simple ways to line up the molecules by requiring only a minimal mechanical "spreading" with a glass rod onto the substrate to orient the LLC systems. In an embodiment, the LLC system comprises an LLC mesophase. In one embodiment, the LLC systems are oriented by spreading the LLC system in one direction.

Subsequent removal of the solvent from the oriented liquid crystal solution can be carried out to form an optically anisotropic film with a thickness in the range of about 0.1 μm to about 2 μm. In an embodiment, the film has a thickness in the range of about 0.2 μm to about 1 μm. In an embodiment, the film has a thickness in the range of about 0.2 μm to about 0.6 μm. In an embodiment, the film has a thickness of about 0.2 μm to about 0.3 μm. In an embodiment, the film has a thickness in the range of about 0.3 μm to about 0.5 μm. In some embodiments, the anisotropic film may also be a polycrystalline film.

To improve substrate wetting and optimization of the rheological properties of a liquid crystal system, the solution can be modified, for example, by adding plasticizing water-soluble polymers and/or anionic or non-ionic surfactants. The LLC system may further comprise one or more water-soluble, low-molecular-weight additives. Each of the additives can be advantageously selected so as not to destroy the alignment properties of the liquid crystal system. Examples of water-soluble, low-molecular-weight additives include, but are not limited to, plasticizing polymer, such as PVA and polyethylene glycol, and anionic or non-ionic surfactants such as those available under the tradename TRITON, which is a nonionic surfactant having hydrophilic polyethylene oxide groups and a hydrocarbon lipophilic or hydrophobic group. These additives may improve substrate wetting and optimize the rheological properties of an LLC system. All additives are preferably selected so as not to destroy the alignment properties of the LLC system.

Embodiments of the films formed from the LLC systems described herein can be generally characterized by an approximately 10% or greater performance advantage, e.g., increase in reproducibility of one or more performance parameters from batch to batch, between different films in the same batch, and over the surface of one film as compared to the other films.

The compounds described herein may be also used to obtain isotropic films. For example, the LLC system comprising a compound having the general structural formula (I) or (II) and a solvent may be applied onto a substrate and not be subjected to any external orienting action. This can be achieved through application of the LLC system by methods such as spraying, offset printing, and silk screening. Removal of the solvent leaves the substrate covered with a polycrystalline film with an overall domain structure that possesses isotropic optical properties.

The lyotropic chromophoric compounds can be used to form at least partially crystalline films and/or polarizing films and/or birefringent films. These lyotropic chromophoric compounds may be used in the production of optically isotropic or anisotropic, polarizing films and/or phase-retarding films and/or birefringent films. In an embodiment, the LLC system used to form an optically isotropic or anisotropic film comprises at least two compounds selected from the general structural formulae (I) and (II). In some embodiments, the LLC system may encompass an aqueous liquid crystal solution that may be referred to as a "water-based ink composition."

In an embodiment, the LLC system is water-based. For example, the LLC system can comprise one or more compounds of the disclosed lyotropic chromophores having the general structural formulae (I) and/or (II) and water. Other solvents can also be used. In an embodiment, the LLC system comprises a mixture of water and an organic solvent miscible with water. In an embodiment, the LLC system comprises a mixture of water and an organic solvent, which is alternatively miscible with water in any proportion or characterized by limited miscibility with water. Useful organic solvents include polar solvents, such as dimethyl sulfoxide (DMSO), dimethylformamide (DMF), alcohol (e.g., methanol or ethanol) and N-Methyl-2-pyrrolidone (NMP).

Other materials known to those having ordinary skill in the art may also be included. In an embodiment, the LLC system further comprises one or more surfactants. In an embodiment, the surfactant is present in an amount of up to about 5% by weight of the LLC system. In an embodiment, the surfactant is present in an amount in the range of about 0.01% to about 3% by weight of the LLC system. In an embodiment, the surfactant is present in an amount in the range of about 0.1% to about 1% by weight of the LLC system. In an embodiment, the LLC system further comprises one or more plasticizers. In an embodiment, the plasticizer is present in an amount of up to about 5% by weight of the LLC system. In an embodiment, the plasticizer is present in an amount in the range of about 0.01% to about 3% by weight of the LLC system. In an embodiment, the plasticizer is present in an amount in the range of about 0.1% to about 1% by weight of the LLC system.

The concentration of the lyotropic chromophoric compound or mixture of lyotropic chromophoric compounds in the LLC systems described herein can vary. In an embodiment, the concentration of the lyotropic chromophoric compound or mixture of lyotropic chromophoric compounds in the LLC systems is in the range of from about 1% to about 70% by weight of the LLC system. In an embodiment, the concentration of the lyotropic chromophoric compound or mixture of lyotropic chromophoric compounds in the LLC systems is about 3% to about 60% by weight of the LLC system. In an embodiment, the concentration of the lyotropic chromophoric compound or mixture of lyotropic chromophoric compounds in the LLC system is in the range of about 5% to about 50% by weight of the LLC system. In an embodiment, the concentration of the lyotropic chromophoric compound or mixture of lyotropic chromophoric compounds in the LLC system is in the range of about 8% to about 40% by weight of the LLC system. In an embodiment, the concentration of the lyotropic chromophoric compound or mixture of lyotropic chromophoric compounds in the LLC system is in the range of about 10% to about 30% by weight of the LLC system. In an embodiment, the concentration of the lyotropic chromophoric compound or mixture of lyotropic chromophoric compounds in the LLC system is in the range of about 7% to about 30% by weight of the LLC system.

The concentration of individual lyotropic chromophoric compounds in the LLC system can also vary, depending on the required properties of the film, as described below. In an embodiment, the LLC system comprises a combination of two or more compounds of the general structural formulae (I) and/or (II), wherein the amount of compound according to formula (I) is in the range of about 0% to about 99% by weight, based on the total amount of chromophoric compounds and the amount of compound according to formula (II) is in the range of about 0% to about 99% by weight, based on the total amount of chromophoric compounds. Optionally, the total amount of compounds according formulae (I) and/or (II) can account for at least 50% of the total weight of chromophoric compounds. Optionally, the total amount of compounds according formulae (I) and/or (II) can account for at least 75% of the total weight of chromophoric compounds. Optionally, the total amount of compounds according formulae (I) and/or (II) can account for at least 90% of the total weight of chromophoric compounds. Optionally, the total amount of compounds according formulae (I) and/or (II) can account for about 100% of the total weight of chromophoric compounds.

In an embodiment, the amount of compound according to formula (I) in the LLC system is in the range of about 1% to about 100% by weight, based on the total amount of chromophoric compounds. In an embodiment, the amount of compound according to formula (I) in the LLC system is in the range of about 5% to about 95% by weight, based on the total amount of chromophoric compounds. In an embodiment, the amount of compound according to formula (I) in the LLC system is in the range of about 10% to about 90% by weight, based on the total amount of chromophoric compounds. In an embodiment, the amount of compound according to formula (I) in the LLC system is in the range of about 20% to about 80% by weight, based on the total amount of chromophoric compounds. In an embodiment, the amount of compound according to formula (I) in the LLC system is in the range of about 1% to about 50% by weight, based on the total amount of chromophoric compounds. In an embodiment, the amount of compound according to formula (I) in the LLC system is in the range of about 50% to about 99% by weight, based on the total amount of chromophoric compounds.

In an embodiment, the amount of compound according to formula (II) in the LLC system is in the range of about 1% to about 100% by weight, based on the total amount of chromophoric compounds. In an embodiment, the amount of compound according to formula (II) in the LLC system is in the range of about 5% to about 95% by weight, based on the total amount of chromophoric compounds. In an embodiment, the amount of compound according to formula (II) in the LLC system is in the range of about 10% to about 90% by weight, based on the total amount of chromophoric compounds. In an embodiment, the amount of compound according to formula (II) in the LLC system is in the range of about 20% to about 80% by weight, based on the total amount of chromophoric compounds. In an embodiment, the amount of compound according to formula (II) in the LLC system is in the range of about 1% to about 50% by weight, based on the total amount of chromophoric compounds. In an embodiment, the amount of compound according to formula (II) in the LLC system is in the range of about 50% to about 99% by weight, based on the total amount of chromophoric compounds.

In an embodiment, a lyotropic liquid crystal system comprises a first compound according to formula (I) or (II), wherein the first compound has a concentration of about 0% to about 50% by mass, and a second compound according to formula (I) or (II) that is different from the first compound, wherein the second compound has a concentration of about 0% to about 50% by mass, wherein the total amount of the first compound and the second compound is up to about 50% by mass, based on the total mass of the LLC system.

Polarized microscopic analysis of the system texture reveals that, with dye concentrations of between about 5% to about 50%, about 5% to about 40%, about 5% to about 30%, or about 7% to about 30% by weight of the LLC system, a stable lyotropic mesophase may be formed at about room temperature. In some embodiments, the stable lyotropic mesophase may be formed at temperatures in the range of from about 10° C. to about 40° C., about 15° C. to about 30° C., or about 20° C. to about 28° C. Accordingly, a nematic phase is observed within a sufficiently wide range of dye concentrations and temperatures. The existence of isotropic phases and their boundaries, as well as two-phase transition regions, have been detected in this system.

In some embodiments, LLC systems described herein further comprise at least one organic dye or substantially colorless compound, which can provide desired optical absorption properties. In an embodiment, the organic dye or substantially colorless organic compound is configured to participate in the formation of a liquid crystal system. In an embodiment, the LLC system further comprises at least one water-soluble organic dye or at least one substantially colorless organic compound. The resulting films can also comprise organic dyes or other organic compounds. In some embodiments, suitable organic dyes or substantially colorless compounds include Brilliant Black BN or Naphthol Blue Black.

Optically anisotropic films of the present invention may be obtained by applying an LLC system described herein onto a substrate, optionally followed by orienting action, and then drying. Illustrative examples describing the synthesis of lyotropic chromophoric compounds, forming LLC system comprising the compounds, and then forming organic films using the LLC system are described in detail below.

In an embodiment, the optically anisotropic film is formed by depositing an LLC system comprising at least one lyotropic chromophoric compound onto a substrate. In an embodiment, the film is at least partially crystalline. In an embodiment, the film further comprises at least one water soluble organic dye. In an embodiment, the film is a polarizing film. In an embodiment, the film is a phase-retarding film.

Another embodiment provides a liquid crystal display comprising at least one E-type polarizer. In an embodiment, the at least one E-type polarizer comprises at least one optically anisotropic film as described herein and a substrate. An embodiment provides a dichroic light-polarizing element comprising a substrate and at least one LLC film as described herein. In some embodiments, the dichroic light-polarizing element is an E-type polarizer. One embodiment provides a liquid crystal active display comprising at least one E-type polarizer film, wherein the E-type polarizer film comprises at least one LLC film as described herein. Conventional LC displays often use O-type films, and the contrast ratio can drop off drastically when the LC display is viewed from an angle off the normal directly. Conversely, a LC display comprising at least one E-type polarizer film may provide wide viewing angles without a substantial drop in contrast ratio. Furthermore, in preferred embodiments the process of making an E-type polarizer comprising an LLC film as described herein can be conducted more easily compared to the conventional process for making O-type polarizers. This also can lead to simplified and lower cost LC devices. The designs and components of a LC display comprising an E-type polarizer are described in more detail in U.S. Pat. No. 7,015,990, which is also incorporated by reference in its entirety, and particularly for the purpose of describing such designs and components.

Another embodiment provides a method of forming an optically anisotropic film. In an embodiment, the method of forming an optically anisotropic film comprises applying an LLC system as described herein onto a substrate, wherein the LLC system comprises a plurality of LLC mesophases, and orienting the plurality of LLC mesophases. In an embodiment, the method further comprises forming the LLC system by mixing at least one chromophoric compound described herein with water or a mixture of water and an organic solvent. In an embodiment, the method comprises drying the LLC system on the substrate. In an embodiment, the orienting of the plurality of LLC mesophases comprises spreading the LLC mesophases in one direction.

In some embodiments, films described herein exhibit high optical anisotropy. For example, polarizer films formed from the compounds of formula (I) and/or formula (II) typically have a dichroic ratio at wavelength corresponding to the main absorption band maximum. The dichroic ratios of such polarizer films are within the range of approximately 9 to about 23 over various wavelengths, which are significantly improved compared to the dyes with sulfonate groups directly attached on the chromophore core (e.g. see comparative examples in Table 1). The increased dichroic ratio provides better contrast ratio for the LCD display application. Additionally, the compounds described herein exhibit improved water solubility and the resultant films also possess high reproducibility over the surface.

In some embodiments, the optically anisotropic films may also be used as double refraction films in various applications.

TABLE 1

Dichroic ratio of the LLC chromophores

| | Structure | $\lambda_{max}$ (nm) | Dichroic ratio |
|---|---|---|---|
| Comparative Example 1 | [structure with $H_4NO_3S$ and $SO_3NH_4$ groups] | 450 | 7 |
| Comparative Example 2 | [structure with $(SO_3NH_4)_n$ group] | 502 | 16 |
| Compound 1 (described below) | [structure with $HO_3S$ and $SO_3H$ groups] | 500 | 23 |

TABLE 1-continued

Dichroic ratio of the LLC chromophores

| | Structure | $\lambda_{max}$ (nm) | Dichroic ratio |
|---|---|---|---|
| Compound 9 (described below) | [structure shown] | 450 | 13 |

Example 1

Synthesis

Synthesis of Compounds of Formulae (I) and (VI)

The following general synthetic scheme (Scheme 1) illustrates a synthetic process by which compounds of formulae (I) and (VI) can be made. However, those having ordinary skill in the art, guided by the disclosure herein, will understand that a similar synthesis can be used to make the trans compounds according to formulae (II) and (VII).

piperazine were added into a stirred melt of phenol at about 70° C. to about 80° C. The mole ratio of the perylene-3,4,9,10-tetracarboxylic dianhydride to o-phenyldiamine derivative to piperazine to phenol was about 1:2.3:3:50. The mixture was heated to a temperature ranging from about 170° C. to 180° C. and kept at this temperature overnight. The water of reaction formed was distilled off as an azeotrope with phenol. After cooling to 130° C., methanol (an equivalent volume with the reaction mixture) was slowly added to the mixture. The mixture was stirred at 60° C. for one hour. The reaction products were then filtered off and washed with methanol

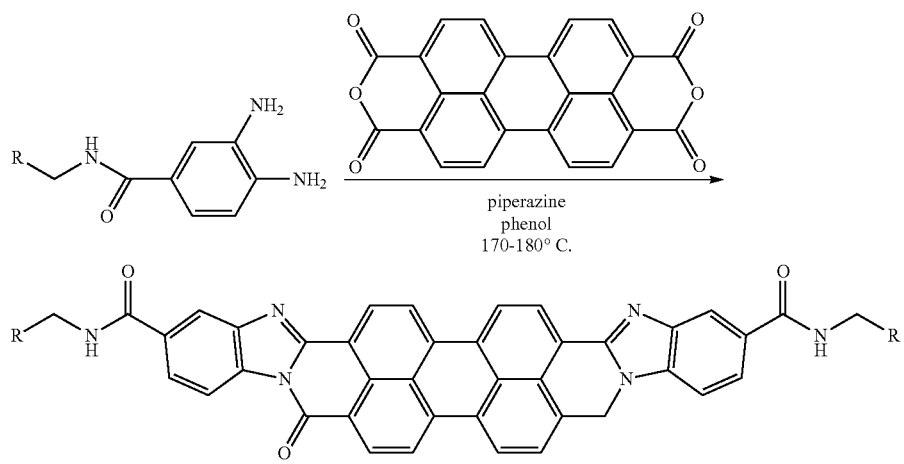

Scheme 1

R in Scheme 1 can vary in the synthesis of the compounds described below. For example, in Compound 1, R is —CH₂CH₂OCH₂CH₂OCH₂CH₂CH₂SO₃H.

until a clear filtrate formed. After drying, a black solid was obtained (70% yield). The pH value of a 0.4% water solution of the black solid product was adjusted to 5.5 to 6.5 by using

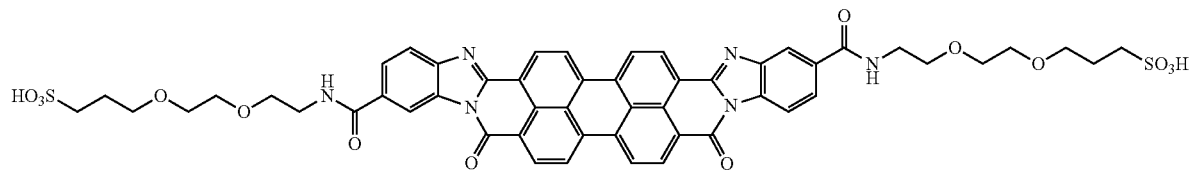

1

Synthesis of Compound 1: A mixture of perylene-3,4,9,10-tetracarboxylic dianhydride, an o-phenyldiamine derivative with R as CH2CH2OCH2CH2OCH2CH2CH2SO3H, and ammonium hydroxide, then desalted and concentrated to a 10% water solution. LCMS (ESI) M–H calculated for C52H46N6O14S2: 1042. found: 1042.

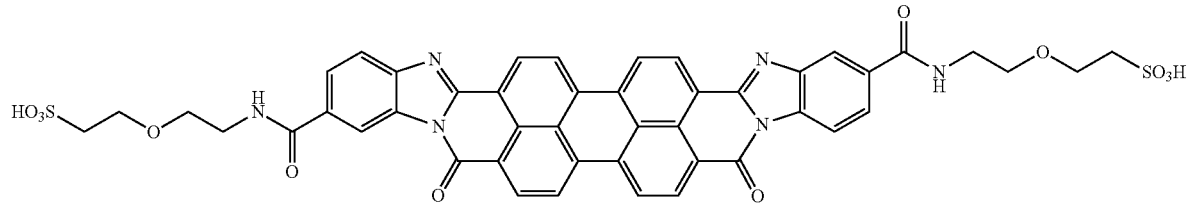

2

Synthesis of Compound 2: Compound 2 was prepared in a similar manner to Compound 1, except R in the o-phenyldiamine derivative was an o-phenyldiamine derivative with R as —CH$_2$CH$_2$OCH$_2$CH$_2$SO$_3$H. LCMS (ESI) M–H calculated for C$_{46}$H$_{34}$N$_6$O$_{12}$S$_2$: 926. found: 926.

(1.43 g, 2.5 mmol), the dianhydride (0.41 g, 1.05 mmol), and piperazine (0.27 g, 3.1 mmol). The resulting solution was heated and stirred at 170° C. overnight. Most of the phenol had crystallized in the neck of the flask, and was separated from the reaction mixture. The reaction mixture was

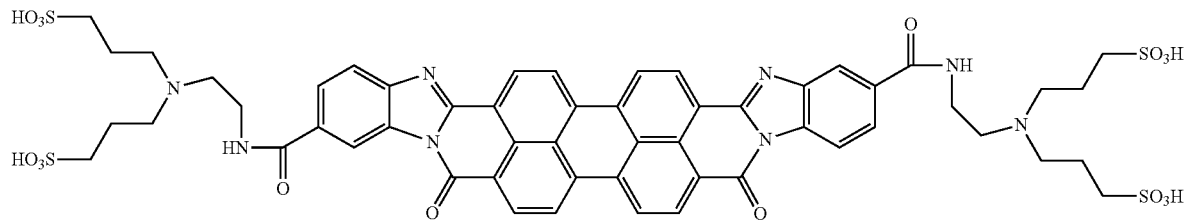

3

Synthesis of Compound 3: Compound 3 was prepared in a similar manner to Compound 1, except R in the o-phenyldiamine derivative was an o-phenyldiamine derivative with R as —CH$_2$CH$_2$N(CH$_2$CH$_2$CH$_2$SO$_3$H)$_2$. For type C LCMS (ESI) M–H calculated for C$_{54}$H$_{52}$N$_8$O$_{16}$S$_4$: 1196. found: 1196.

extracted with water, filtered to remove solids, and the filtrate was washed with ethyl acetate to remove residual phenol and piperazine. The remaining aqueous solution was "desalted" through a reverse osmosis (RO) membrane to remove piperazine and unreacted diamine. The resulting aqueous solution

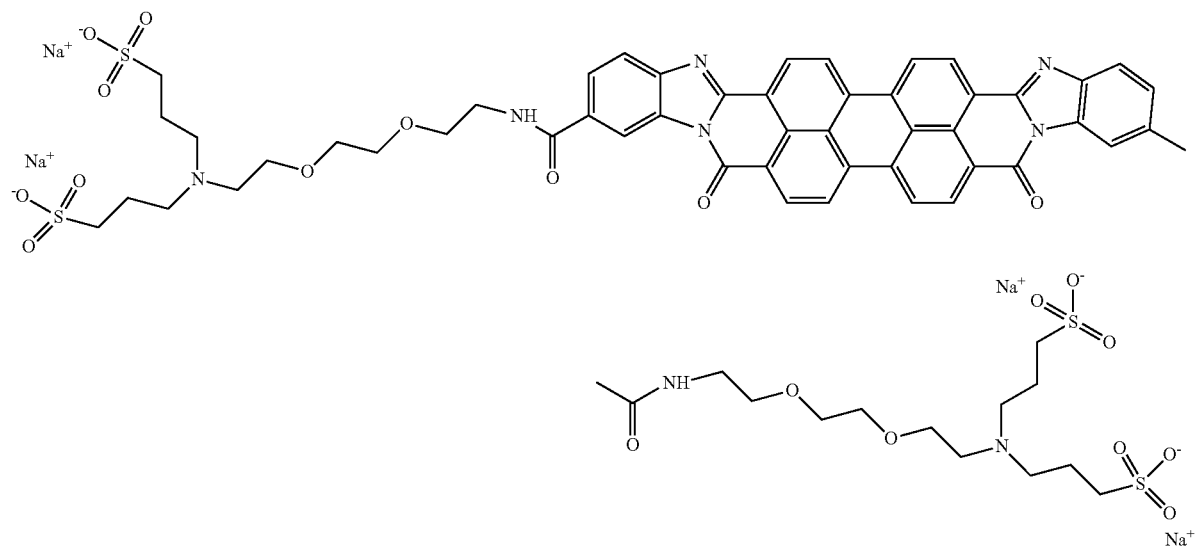

4

Synthesis of Compound 4: To a solution of melted phenol was added an o-phenyldiamine derivative with R represented by —CH$_2$CH$_2$OCH$_2$CH$_2$OCH$_2$CH$_2$N(CH$_2$CH$_2$CH$_2$SO$_3$H)$_2$ was concentrated to 10 wt % to yield 1.3 g of product (97% yield). LC-MS (M–2H; calculated for C$_{62}$H$_{64}$N$_{10}$O$_{20}$S$_4^{--}$= 1370.3. found: 685, M–3H=457).

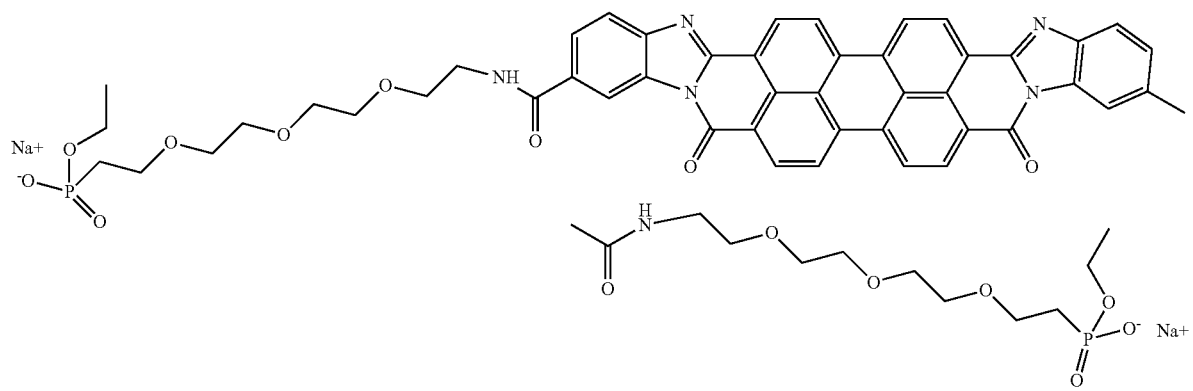

Synthesis of Compound 5: Compound 5 was prepared in a similar manner as Compound 4, except the o-phenyldiamine derivative had an R of —CH$_2$CH$_2$OCH$_2$CH$_2$OCH$_2$CH$_2$OCH$_2$CH$_2$P(OCH$_2$CH$_3$)O$_2$H. The final product was purified by prep HPLC on C-18 with triethylammonium acetate buffer to yield a triethylammonium salt. LCMS (calculated for M−2H, C$_{58}$H$_{58}$N$_6$O$_{16}$P$_{22}^-$=1156.3. found: 578).

Synthesis of Compounds of Formulae (II) and (VII)

The following general synthetic scheme (Scheme 2) illustrates a synthetic process by which compounds of formulae (II) and (VII) can be made. However, those having ordinary skill in the art, guided by the disclosure herein, will understand that a similar synthesis can be used to make the trans compounds according to formulae (I) and (VI).

Scheme 2

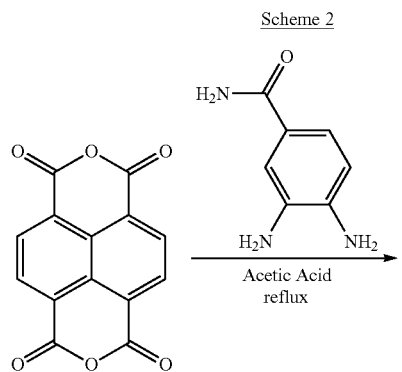

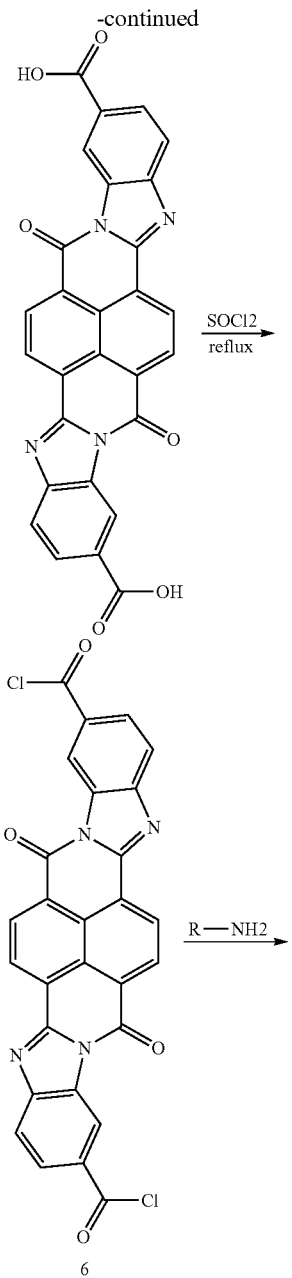

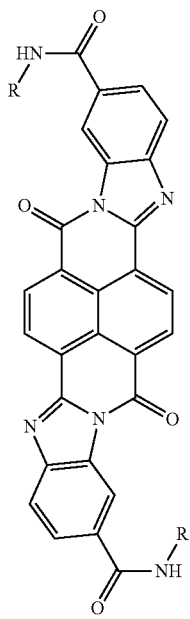

Synthesis of Compound 6 (bis-acid chloride): A mixture of napthalene-1,2,5,6-tetracarboxylic acid anhydride (20.0 g, 74.6 mmol) and 3,4-diaminobenzoic acid (34.0 g, 22.4 mmol) were suspended in 600 mL of acetic acid and heated at reflux for 3 days. The reaction mixture was cooled to room temperature, and the solids were collected by filtration and washed with water. The solids were suspended in water which was made basic with 200 mmol of sodium hydroxide. Residual solids were removed by centrifugation. The dark solution was brought to pH 3.7 with concentrated hydrochloric acid. The resulting solids were collected by centrifugation and rinsed with 1:1 methanol/water. Solids were dried under vacuum to yield 32.4 g (87%) of the diacid. UV-max (456). FT-IR (solid) show strong C=O stretch for the acid at 1682 cm$^{-1}$. LC-MS (M−H)=499. $^1$H NMR(CF3CO2D, 400 MHz) 10.18 (bs, 1H), 9.93 (bs, 2H), 9.78 (bs, 2H), 9.55-9.63 (m, 1H), 9.38-9.45 (m, 1H), 9.16-9.27 (m, 2H), 8.78-8.86 (m, 1H).

The diacid was suspended in thionyl chloride and heated at reflux for 3 days. The mixture was cooled and the excess thionyl chloride was removed in vacuo. The solids were suspended in xylenes and dried by rotary evaporation (three times) to remove residual thionyl chloride. Formation of the acid chloride was evidenced by shifting of C=O band to a higher frequency (1691 cm$^{-1}$) and disappearance of broad O—H stretch (1700-3700 cm-1).

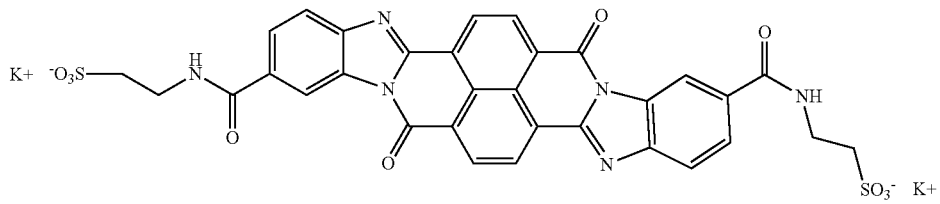

7

Synthesis of Compound 7: A solution was prepared by dissolving 2-aminoethanesulfonic acid (9.5 mmol, 1.7 g) and potassium hydroxide (9.5 mmol, 0.53 g) in 100 mL of water. The initial pH of the solution was measured at 9.6. The bis-acid chloride (Compound 6, 3.1 mmol, 1.7 g) was added to the mixture and the resulting mixture is stirred. After stirring for about 90 to 180 minutes, the of the mixture is adjusted to 9.5 with 1M potassium hydroxide. The resulting mixture was then allowed to stir for 3 days. The mixture was diluted to 190 mL with water, and the solid precipitate was removed by centrifugation. The filtrate was desalted on a membrane and reduced under vacuum to 8 w/w % in water. Yield (1.4 g, 58%). LC-MS analysis (M−2H=356).

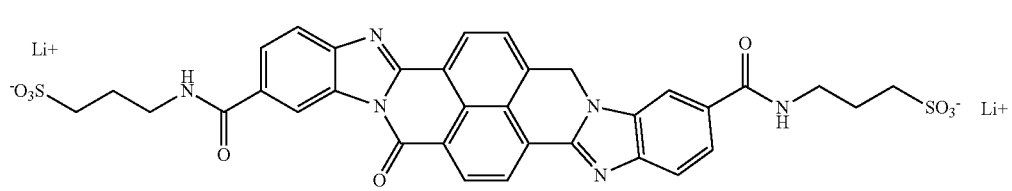

8

Synthesis of Compound 8: 3-amino-1-propane sulfonic acid (36.9 mmol, 5.14 g) was dissolved in 100 mL of water. The solution was brought to pH 9.9 with 18 mL of 1M LiOH. The bis-acid chloride (Compound 6) was added to the solution and the mixture stirred for 3 hours. Another 7 mL of 1M LiOH was added to raise the pH from 8.8 to 9.4 and the mixture continued stirring overnight. The pH dropped to 1.6 overnight. Another 18 mL of 1 M LiOH was added to raise the pH to 9.3, and the mixture stirred for 2 more hours. The pH was adjusted to 2.5 with 1M HCl, and the solids were removed by filtration. Excess salts were removed via a RO membrane, and the solution concentrated under vacuum to 7.5 wt %. Yield (4.9 g as solid, 70%). LCMS (M–H=741).

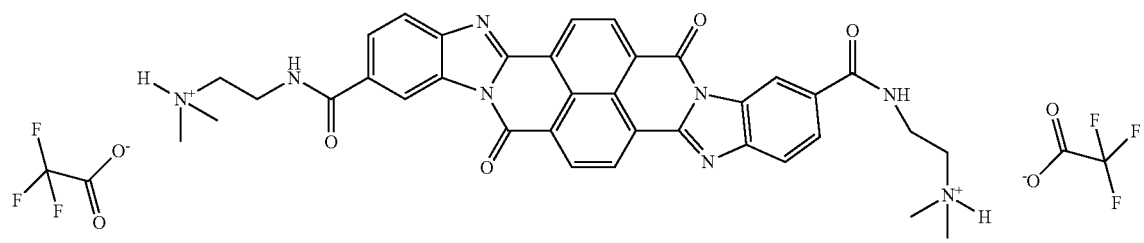

9

Synthesis of Compound 9: The bis-diacid chloride, Compound 6, (10.4 g, 18.4 mmol) was added in portions to neat N,N-dimethyl ethylenediamine (100 g, 1.13 moles) while stirring. The resulting dark mixture was stirred overnight. The excess amine was removed under vacuum at 80° C. The residue was taken up in 2 liters of water and made acidic (pH<1) with concentrated hydrochloric acid. Solids were removed by filtration through celite. Excess salts were removed through a RO membrane. The solution was concentrated to 10.2 wt %. Yield of product (as HCl salt) was 11.5 grams (88% of theory). A portion of the hydrochloride salt was converted to trifluoroacetate salt by first removing the water under vacuum, then repeatedly dissolving the solid residue in trifluoroacetic acid and drying by rotary evaporation. The final trifluoroacetate salt showed no precipitate when mixed with Ag(I). LCMS (M–H=641).

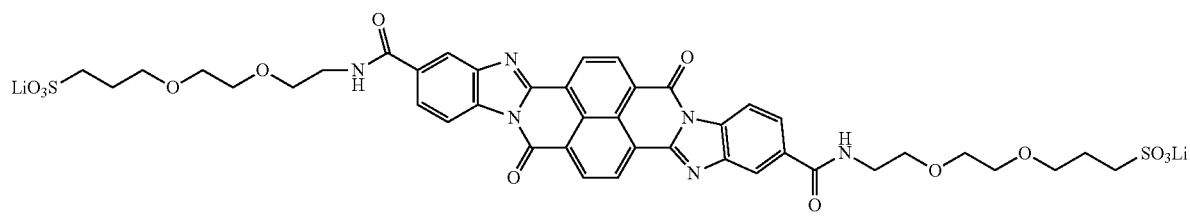

10

Synthesis of Compound 10: 9-amino-4,7-dioxanonane sulfonic acid (4.1 mmol, 1.17 g) was suspended in 15 mL of DMF at 60° C. Triethylamine (1.8 mL, 13.1 mmol) was added to the mixture with stirring. The bis-acid chloride Compound 6 (1.0 g, 1.86 mmol) was added in portions then stirred overnight. Most of the DMF was removed under vacuum, and the residue was taken up in water. Insolubles were removed by filtration. The filtrate was concentrated under vacuum, and purified by prep HPLC on a C-18 column with $Et_3NH^+Cl^-$ buffer, followed by a final desalt process through RO membrane to remove residual mobile phase buffer. LCMS (M–2H=458).

Synthesis of Compounds of Formula (I) and (II)

The following general synthetic scheme (Scheme 3) illustrates a synthetic process by which compounds of formulae (II) and (XV) can be made. However, those having ordinary skill in the art, guided by the disclosure herein, will understand that a similar synthesis can be used to make the cis compounds according to formula (I) and (XIV).

Scheme 3
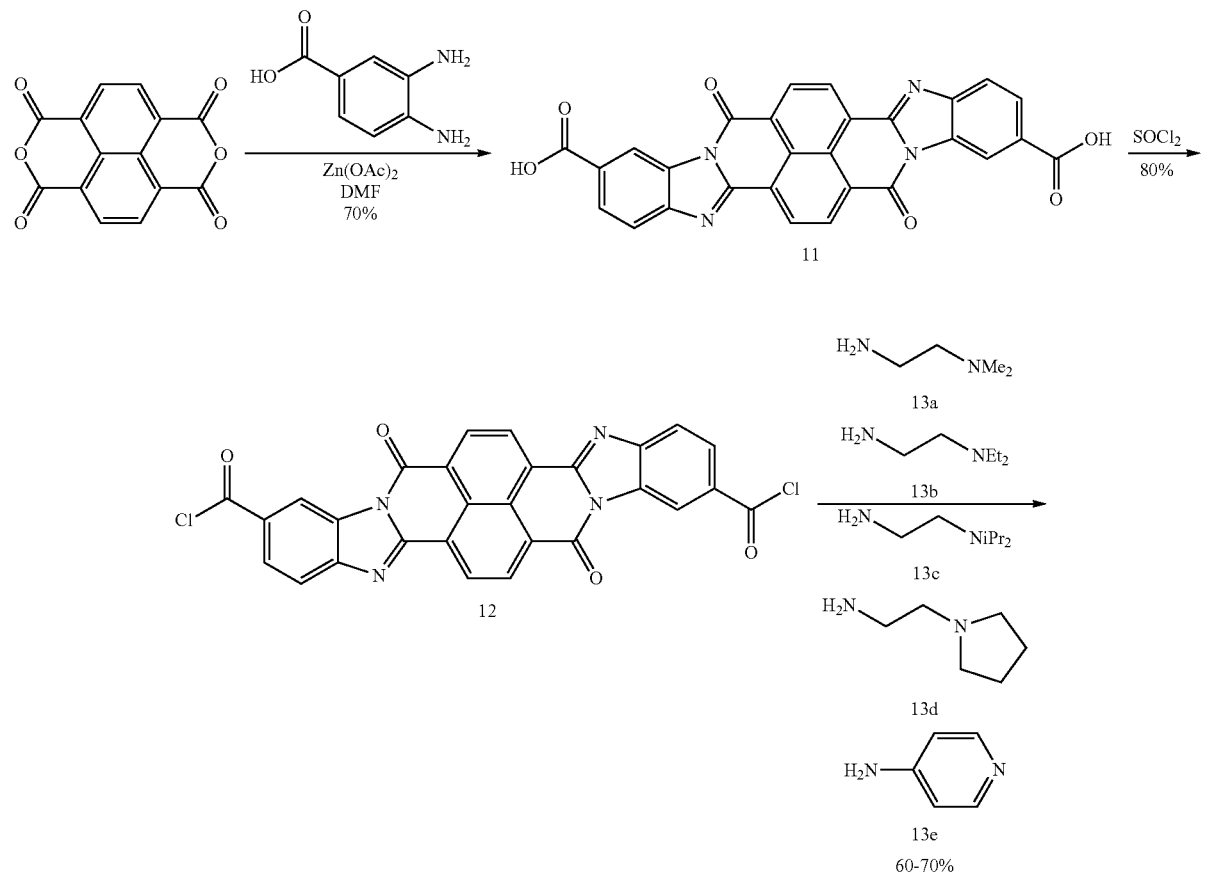
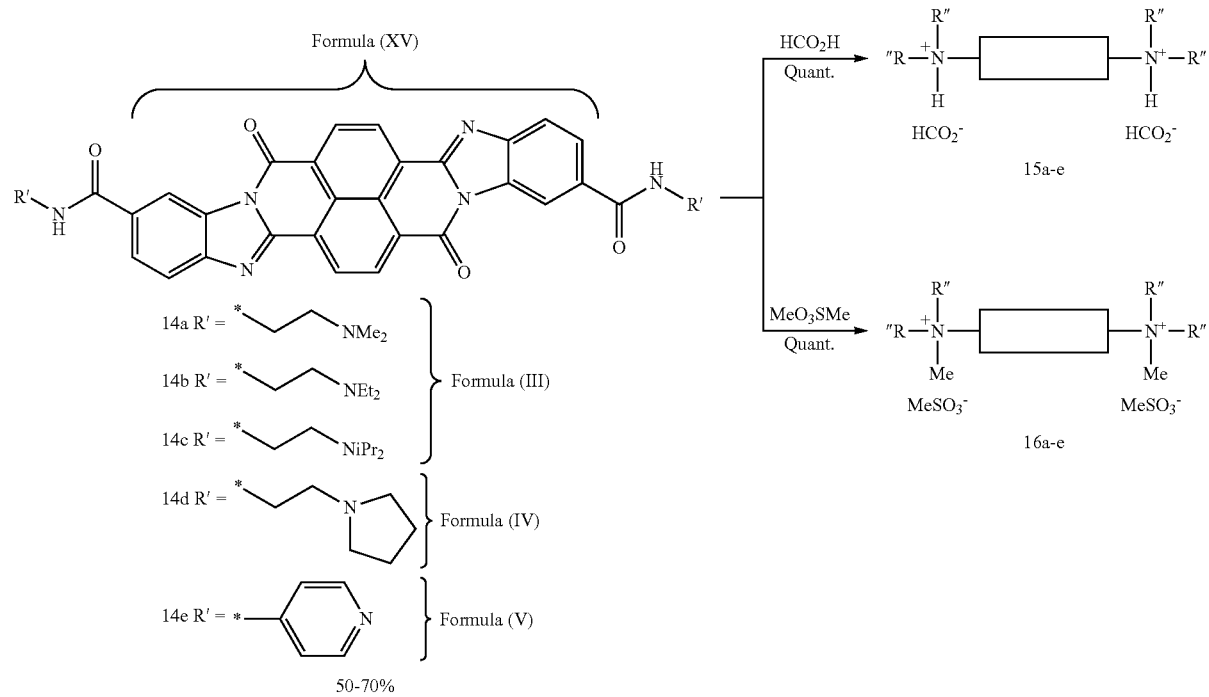

Each R" in Scheme 3 can be determined in accordance with its associated R'. For example, where R' is —$CH_2CH_2N(Me)_2$ in Compound 14a, then each of the R" in Compounds 15a and 16a is —$CH_3$. The two R" in each compound are also capable of forming a ring (see 14d-16d and 14e-16e).

Synthesis of Compound 11: 1,4,5,8-Naphthalene-tetracarboxylic dianhydride (2.68 g, 10 mmol), 3,4-diaminobenzoic acid (3.05 g, 20 mmol), zinc acetate (183 mg, 1.0 mmol), and 20 mL of DMF were heated in a microwave oven for 2 hours at 145° C., or alternatively at 125-140° C. in DMF for 5 hrs or N-methylpyrrolidinone overnight. After cooling, the mixture was diluted with 200 mL of DI water and stirred for an additional 10 minutes. The brownish-red suspension was separated by filtration then washed thoroughly with water (10×) to completely remove DMF. Drying in vacuo at 60° C. for two hours yielded with 4.9 g (90%) of solid, >90% purity by NMR. $^1$H NMR (400 MHz, $D_2SO_4$): δ 10.2 (d, 2H), 9.95 (dd, 2H), 9.8 (dd, 2H), 9.23 (m, 2H), 8.81 (m, 2H).

Synthesis of Compound 12: Carboxylic acid derivative 11 (2.0 g, 4.0 mmol) was heated at reflux in neat thionyl chloride (20 mL) for 5 hours. The excess $SOCl_2$ was removed by distillation to yield the acid chloride 12 as bright reddish powder which was used without further purification.

Synthesis of Compounds 14a-e (general procedure): To 4.0 mmol of acid chloride 12 was added 20 mL of DMF, 10 mL (72 mmol) of triethylamine, and N,N-dimethylethylenediamine (13a) (2.65 mL, 24 mmol). The reaction mixture was heated for 5 hours at 100° C. after which the solvent and excess reagents were removed in vacuo. To the residue was added in 1 L of DI water and the solution was subjected to tangential flow filtration (with 5 kDa) filter until the conductivity of the permeate reached 30-35 μS. The water was removed in vacuo to give 1.8 g (70%) of compound 14a. MS (ESI): m/z=641 [M+H]$^+$ (100%) for $C_{36}H_{32}N_8O_4$. Compound 14b. MS (ESI): m/z=697 M$^+$ (100%) for $C_{40}H_{40}N_8O_4$. Compound 14c (56%). MS (ESI): m/z=753 M$^+$ (100%) for $C_{44}H_{48}N_8O_4$. Compound 14d (66%). MS (ESI): m/z=693 M$^+$ (100%) for $C_{40}H_{36}N_8O_4$. Compound 14e (60%). MS (ESI): m/z=652 M$^+$ (100%) for $C_{38}H_{20}N_8O_4$. Substituting compound 13a with compounds 13b-13e in the reaction produced compounds 14b-14e, respectively.

Synthesis of Compounds 15a-e (general procedure): To 1 g of diaamine 14a was added formic acid (50 mL), followed by sonication and slight heating. Excess of formic acid was removed in vacuo, and the process was repeated 2-3 times, giving rise to protonated 15a as shiny, black residue in quantitative yield. To the residue was added in 1 L of DI water and the solution was subjected to tangential flow filtration (with 5 kDa) filter until the conductivity of the permeate reached 30-35 μS. The water was removed in vacuo to give 800 mg (70%) of compound 15a. MS (ESI): m/z=643 [M]$^+$ (100%) for $C_{36}H_{34}N_8O_4$. Substituting compound 14a with compounds 14b-14e in the reaction produced compounds 15b-15e, respectively.

Synthesis of Compounds 16a-e (general procedure): To 1 g of diamine 14a was added 10 eq methoxy mesylate and the solution was refluxed for 15 minutes. The reaction was then cooled and 1 L DI water was added, and the solution was subjected to tangential flow filtration (with 5 kDa) filter until the conductivity of the permeate reached 30-35 μS. The water was removed in vacuo to give 900 mg (67%) of compound 16a. MS (ESI): m/z=671 [M]$^+$ (100%) for $C_{38}H_{38}N_8O_4$. Substituting compound 14a with compounds 14b-14e in the reaction produced compounds 16b-16e, respectively.

Example 2

Measurement of Dichroic Ratios

Sample 1 was prepared by dissolving 150 mg of Compound 1 in 10 mL of deionized water, titrating with 5% triethylamine solution to pH=7 and concentrating to 12 wt % using a rotavaporator. The resulting solution was coated onto a standard glass slide (2 inches by 3 inches by 1 mm, previously washed with 1% alcohol solution in an ultrasonic tank for 20 minutes and later rinsed with deionized water, isopropyl alcohol and dried in room temperature) with an applicator rod (⅜ inch in diameter, #2½ wire size, Paul N. Gardner Co. Inc.) at a linear velocity of 25 mm/s. The resulting film thickness was approximately 0.2 μm. The process was conducted at room temperature (~20° C.) and relative humidity of 65% after the film was dried under the same condition.

The film was characterized by absorbance spectra measured on a Perkin Elmer Lamda Bio 40 UV/Vis Spectrum spectrophotometer in a wavelength range from 380 to 800 nm using a light beam polarized along the direction of the film application ($A_{par}$) and the direction perpendicular to that ($A_{per}$). The dichroic ratio $K_d$=log(Apar)/log(Aper) was equal to about 23 at about 500 nm.

Sample 2 was prepared by dissolving 150 mg of Compound 2 in 10 mL of deionized water, titrating with 5% LiOH solution to pH=7 and concentrating to 8 wt % using a rotavaporator. This solution was coated onto a standard glass slide by the same technique described for Sample 1. The resulting film thickness was approximately 0.2

The film was characterized by absorbance spectra measured on a spectrophotometer in a wavelength range from 380 to 800 nm using a light beam polarized along the direction of the film application ($A_{par}$) and the direction perpendicular to that ($A_{per}$). The dichroic ratio ($K_d$) was equal to about 11 at about 500 nm.

Sample 3 was prepared by dissolving 150 mg of Compound 3 in 10 mL of deionized water, titrating with 5% LiOH solution to pH=7 and concentrating to 15 wt % using a rotavaporator. This solution was coated onto a standard glass slide by the same technique described for Sample 1. The resulting film thickness was approximately 0.2 μm.

The film was characterized by absorbance spectra measured on a spectrophotometer in a wavelength range from 380 to 800 nm using a light beam polarized along the direction of the film application ($A_{par}$) and the direction perpendicular to that ($A_{per}$). The dichroic ratio ($K_d$) was equal to about 17 at about 500 nm.

Sample 4 was prepared by dissolving 150 mg of Compound 4 in 10 mL of deionized water, titrating with 5% NaOH solution to pH=7 and concentrating to 15 wt % using a rotavaporator. This solution was coated onto a standard glass slide by the same technique described for Sample 1. The resulting film thickness was approximately 0.2 vtm.

The film was characterized by absorbance spectra measured on a spectrophotometer in a wavelength range from 380 to 800 nm using a light beam polarized along the direction of the film application ($A_{par}$) and the direction perpendicular to that ($A_{per}$). The dichroic ratio ($K_d$) was equal to about 17 at about 500 nm.

Sample 5 was prepared by dissolving 150 mg of Compound 5 in 10 mL of deionized water, titrating with 5% NaOH solution to pH=7 and concentrating to 12 wt % using a rotavaporator. This solution was coated onto a standard glass slide by the same technique described for Sample 1. The resulting film thickness was approximately 0.2 μm.

The film was characterized by absorbance spectra measured on a spectrophotometer in a wavelength range from 380 to 800 nm using a light beam polarized along the direction of the film application ($A_{par}$) and the direction perpendicular to that ($A_{per}$). The dichroic ratio ($K_d$) was equal to about 17 at about 500 nm.

Sample 6 was prepared by dissolving 150 mg of Compound 7 in 10 mL of deionized water, titrating with 5% KOH solution to pH=7 and concentrating to 8 wt % using a rotavaporator. This solution was coated onto a standard glass slide by the same technique described for Sample 1. The resulting film thickness was approximately 0.2

The film was characterized by absorbance spectra measured on a spectrophotometer in a wavelength range from 380 to 800 nm using a light beam polarized along the direction of the film application ($A_{par}$) and the direction perpendicular to that ($A_{per}$). The dichroic ratio ($K_d$) was equal to about 8 at about 450 nm.

Sample 10 was prepared by dissolving 150 mg of Compound 15a in 2 mL of deionized water and then concentrating to 17 wt % using a rotary evaporator. The resulting solution was coated onto a standard glass slide (2 inches by 3 inches by 1 mm, previously washed with 1% alcohol solution in an ultrasonic tank for 60 minutes and later rinsed with deionized water, isopropyl alcohol and dried in room temperature) with an applicator rod (⅜ inch in diameter, #1½ wire size, Paul N. Gardner Co. Inc.) at a linear velocity of 25 mm/s. The resulting film thickness was approximately 200 nm. The process was conducted at room temperature (~20° C.) and relative humidity of 65% after the film was dried under the same condition.

The film was characterized by absorbance spectra measured on a spectrophotometer in a wavelength range from 380 to 780 nm using a light beam polarized along the direction of the film application ($A_{par}$) and the direction perpendicular to that ($A_{per}$). The dichroic ratio ($K_d$) was equal to about 12 at about 454 nm.

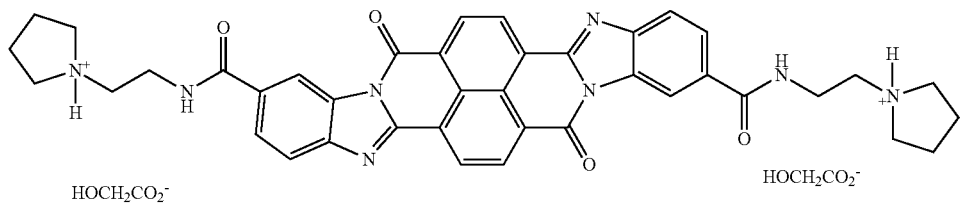

(Compound 17d)

Sample 7 was prepared by dissolving 150 mg of Compound 8 in 10 mL of deionized water, titrating with 5% LiOH solution to pH=7 and concentrating to 8 wt % using a rotavaporator. This solution was coated onto a standard glass slide by the same technique described for Sample 1. The resulting film thickness was approximately 0.2 µm.

The film was characterized by absorbance spectra measured on a spectrophotometer in a wavelength range from 380 to 800 nm using a light beam polarized along the direction of the film application ($A_{par}$) and the direction perpendicular to that ($A_{per}$). The dichroic ratio ($K_d$) was equal to about 10 at about 450 nm.

Sample 8 was prepared by dissolving 150 mg of Compound 9 in 10 mL of deionized water and then concentrating to 8 wt % using a rotavaporator. This solution was coated onto a standard glass slide by the same technique described for Sample 1. The resulting film thickness was approximately 0.2 µm.

The film was characterized by absorbance spectra measured on a spectrophotometer in a wavelength range from 380 to 800 nm using a light beam polarized along the direction of the film application ($A_{par}$) and the direction perpendicular to that ($A_{per}$). The dichroic ratio ($K_d$) was equal to about 13 at about 450 nm.

Sample 9 was prepared by dissolving 150 mg of Compound 10 in 10 mL of deionized water and then concentrating to 8 wt % using a rotavaporator. This solution was coated onto a standard glass slide by the same technique described for Sample 1. The resulting film thickness was approximately 0.2 µm.

The film was characterized by absorbance spectra measured on a spectrophotometer in a wavelength range from 380 to 800 nm using a light beam polarized along the direction of the film application ($A_{par}$) and the direction perpendicular to that ($A_{per}$). The dichroic ratio ($K_d$) was equal to about 9 at about 450 nm.

Compound 17d was prepared in the same manner as Compound 15d above, except that glycolic acid was used instead of formic acid to make the ammonium salt. Sample 11 was prepared by dissolving 150 mg of Compound 17d in 2 mL of deionized water and then concentrating to 25 wt % using a rotary evaporator. This solution was coated onto a standard glass slide by the same technique described for Sample 10. The resulting film thickness was approximately 200 nm.

The film was characterized by absorbance spectra measured on a spectrophotometer in a wavelength range from 380 to 780 nm using a light beam polarized along the direction of the film application ($A_{par}$) and the direction perpendicular to that ($A_{per}$). The dichroic ratio ($K_d$) was equal to about 4 at about 470 nm.

Sample 12 was prepared by dissolving 150 mg of Compound 16e in 5 mL of deionized water and concentrating to 18 wt % using a rotary evaporator. This solution was coated onto a standard glass slide by the same technique described for Sample 10. The resulting film thickness was approximately 200 nm.

The film was characterized by absorbance spectra measured on a spectrophotometer in a wavelength range from 380 to 780 nm using a light beam polarized along the direction of the film application ($A_{par}$) and the direction perpendicular to that ($A_{per}$). The dichroic ratio ($K_d$) was equal to about 3 at about 460 nm.

The above description discloses several methods and materials of the preferred embodiments. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A lyotropic chromophoric compound represented by the general structural formulae (I) or (II), or a salt thereof:

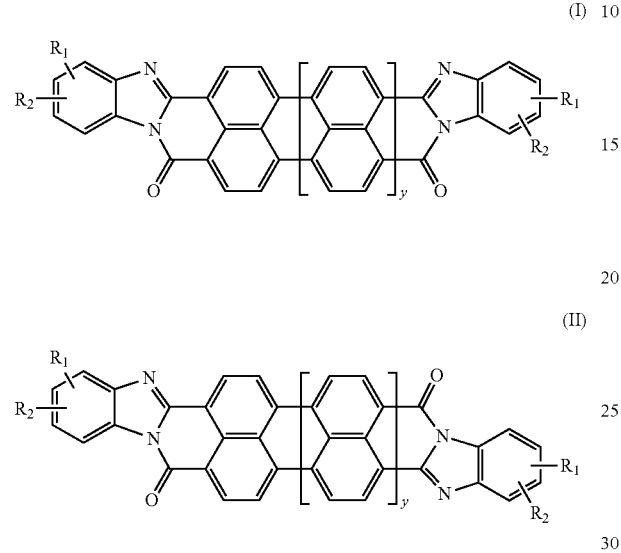

wherein y is an integer in the range from 0 to about 4; each $R_1$ and $R_2$ is independently selected from the group consisting of —H, —OH, —NH$_2$, —Br, —I, —NO$_2$, —F, —CF$_3$, —CN, —COOH, —CONH$_2$, optionally substituted $C_1$ to $C_6$ alkyl, optionally substituted $C_2$ to $C_6$ acetyl, optionally substituted $C_6$ to $C_{10}$ aryl, optionally substituted $C_2$ to $C_6$ alkynyl, optionally substituted $C_2$ to $C_6$ alkenyl, optionally substituted $C_1$ to $C_6$ alkoxyl, optionally substituted $C_1$ to $C_6$ alkylamino, -L$_1$-(M$_1$)$_r$, -L$_2$-(M$_2$)$_s$, and the following formulae (III), (IV), and (V):

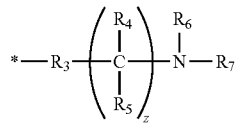

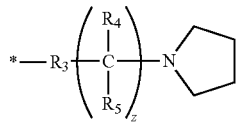

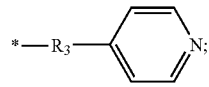

provided that at least one of $R_1$ and $R_2$ is selected from the group consisting of -L$_1$-(M$_1$)$_r$, -L$_2$-(M$_2$)$_s$, and the formulae (III), (IV), and (V);

wherein L$_1$ and L$_2$ each independently represent a hydrophilic linker; each M$_1$ and M$_2$ independently represent an acidic group, a basic group, or salt thereof; each r is independently 1 or 2; each s is independently 1 or 2; R$_3$ is independently represented by —NH—, —CONH—, —O— or —COO—; R$_4$, R$_5$, R$_6$, and R$_7$ are each independently selected from the group consisting of hydrogen, an optionally substituted $C_1$ to $C_6$ alkyl group, an optionally substituted $C_2$ to $C_6$ alkenyl group, an optionally substituted $C_2$ to $C_6$ alkynyl group, an optionally substituted $C_1$ to $C_6$ alkyl group substituted with at least one hydroxyl group, an optionally substituted $C_3$ to $C_8$ cycloalkyl group, an optionally substituted $C_6$ to $C_{10}$ aryl group, and an optionally substituted $C_7$ to $C_{16}$ aralkyl group; and, z is an integer in the range of 0 to about 4.

2. The compound of claim 1, represented by the structural formulae (VI) or (VII):

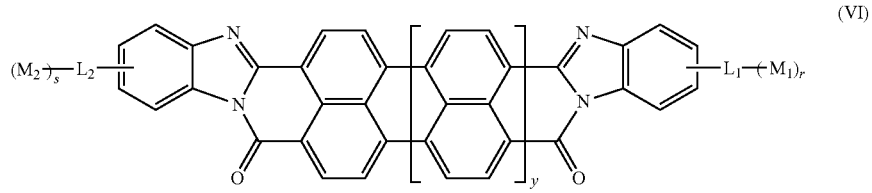

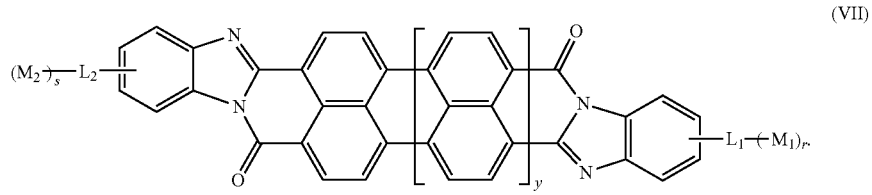

3. The compound of claim 2, wherein either or both of $L_1$ and $L_2$ is independently selected from a linker that comprises the general structural formula (VIII), a linker that comprises the general structural formula (IX) and a linker that comprises the general structural formula (X):

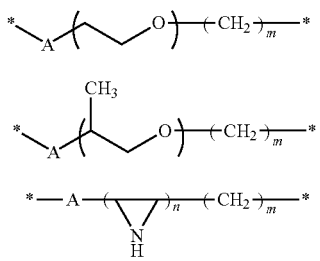

wherein each A independently represents a bond or is selected from the group consisting of:

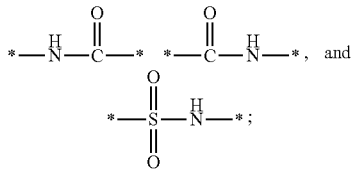

each n is independently an integer in the range of 0 to about 9; and each m is independently an integer in the range of 0 to about 6, provided that at least one of n or m is at least 1.

4. The compound of claim 2, wherein either or both of $L_1$ and $L_2$ is independently selected from a linker that comprises the general structural formula (XI), a linker that comprises the general structural formula (XII) and a linker that comprises the general structural formula (XIII):

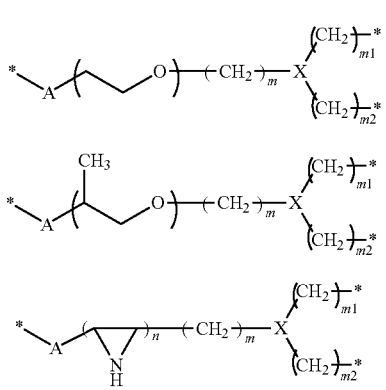

wherein each X independently represents N or P, each A independently represents a bond or is selected from the group consisting of:

-continued

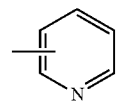

each n is independently an integer in the range of 0 to about 9; and each m, m1, and m2 is independently an integer in the range of 0 to about 6, provided that at least one of n or m is at least 1.

5. The compound of claim 2, wherein each $M_1$ and $M_2$ independently comprises a moiety selected from —$CONH_2$, —COOH, —$SO_3H$, —SH, —$NR_8R_9$, —$PO(OH)_2$, —$PO(OR')(OH)$, —$PO(OR')_2$, —OH, and the following structure:

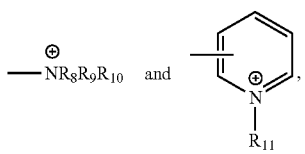

wherein R', $R_8$, and $R_9$ are each independently selected from hydrogen, an optionally substituted $C_1$ to $C_6$ alkyl group, an optionally substituted $C_2$ to $C_6$ alkenyl group, an optionally substituted $C_2$ to $C_6$ alkynyl group, an optionally substituted $C_3$ to $C_8$ cycloalkyl group, an optionally substituted $C_6$ to $C_{10}$ aryl group, and an optionally substituted $C_7$ to $C_{16}$ aralkyl group.

6. The compound of claim 2, wherein each $M_1$ and $M_2$ is independently selected to comprise an anion portion independently selected from —$PO_3^{2-}$, —$PO(OR')O^-$, —$SO_3^-$, and —$CO_2^-$, wherein R' is selected from hydrogen, an optionally substituted $C_1$ to $C_6$ alkyl group, an optionally substituted $C_2$ to $C_6$ alkenyl group, an optionally substituted $C_2$ to $C_6$ alkynyl group, an optionally substituted $C_3$ to $C_8$ cycloalkyl group, an optionally substituted $C_6$ to $C_{10}$ aryl group, and an optionally substituted $C_7$ to $C_{16}$ aralkyl group.

7. The compound of claim 2, wherein each $M_1$ and $M_2$ is independently selected to comprise a cation portion selected from:

wherein $R_8$, $R_9$, $R_{10}$, and $R_{11}$ are each independently selected from hydrogen, an optionally substituted $C_1$ to $C_6$ alkyl group, an optionally substituted $C_2$ to $C_6$ alkenyl group, an optionally substituted $C_2$ to $C_6$ alkynyl group, an optionally substituted $C_3$ to $C_8$ cycloalkyl group, an optionally $C_6$ to $C_{10}$ aryl group, and an optionally substituted $C_7$ to $C_{16}$ aralkyl group.

8. The compound of claim 7, wherein $R_8$, $R_9$, $R_{10}$, and $R_{11}$ are each independently selected from hydrogen, methyl, ethyl, n-propyl, isopropyl, n-butyl, isobutyl, sec-butyl, tert-butyl, and cyclohexyl.

9. The compound of claim 2, wherein each $M_1$ and $M_2$ further comprise a counter ion.

10. The compound of claim 9, wherein the counter ion is independently selected from $H^+$, $NH_4^+$, $NH(Et)_3^+$, $K^+$, $Li^+$, $Na^+$, $Cs^+$, $Ca^{++}$, $Sr^{++}$, $Mg^{++}$, $Ba^{++}$, $Co^{++}$, $Mn^{++}$, $Zn^{++}$, $Cu^{++}$, $Pb^{++}$, $Fe^{++}$, $Ni^{++}$, $Al^{3+}$, $Ce^{3+}$, and $La^{3+}$.

11. The compound of claim 9, wherein the counter ion is independently selected from $CO_2CF_3^-$, $CH_3SO_3^-$, $Cl^{-1}$, $Br^-$, and $I^-$.

12. The compound of claim 9, wherein one or more counter ions are shared by at least two molecules.

13. The compound of claim 1 wherein y is 0.

14. The compound of claim 13, represented by the general structural formulae (XIV) or (XV), or a salt thereof:

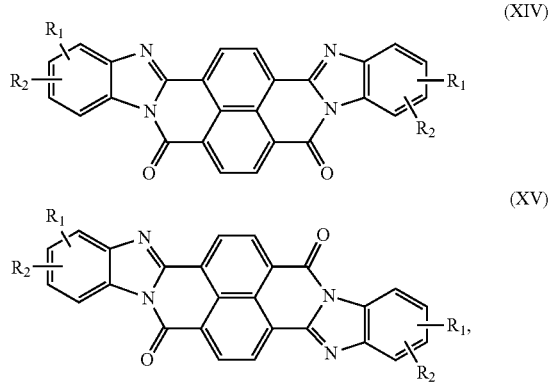

wherein each $R_1$ and $R_2$ is independently selected from the group consisting of —H, —OH, —$NH_2$, —Cl, —Br, —I, —$NO_2$, —F, —$CF_3$, —CN, —COOH, —$CONH_2$, optionally substituted $C_1$ to $C_6$ alkyl, optionally substituted $C_2$ to $C_6$ acetyl, optionally substituted $C_6$ to $C_{10}$ aryl, optionally substituted $C_2$ to $C_6$ alkynyl, optionally substituted $C_2$ to $C_6$ alkenyl, optionally substituted $C_1$ to $C_6$ alkoxyl, optionally substituted $C_1$ to $C_6$ alkylamino, and the following formulae (III), (IV), and (V):

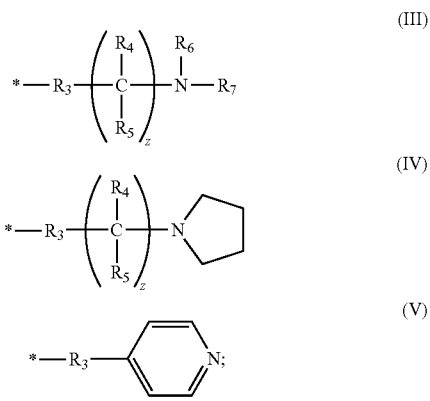

provided that at least one of $R_1$ and $R_2$ is selected from the group consisting of the formulae (III), (IV), and (V);
wherein $R_3$ is independently represented by —NH—, —CONH—, —O— or —COO—; $R_4$, $R_5$, $R_6$, and $R_7$ are each independently selected from the group consisting of hydrogen, an optionally substituted $C_1$ to $C_6$ alkyl group, an optionally substituted $C_2$ to $C_6$ alkenyl group, an optionally substituted $C_2$ to $C_6$ alkynyl group, an optionally substituted $C_1$ to $C_6$ alkyl group substituted with at least one hydroxyl group, an optionally substituted $C_3$ to $C_8$ cycloalkyl group, an optionally substituted $C_6$ to $C_{10}$ aryl group, and an optionally substituted $C_7$ to $C_{16}$ aralkyl group; and, z is an integer in the range of 0 to about 4.

15. The compound of claim 14, wherein $R_4$, $R_5$, $R_6$, and $R_7$ are each independently selected from the group consisting of hydrogen, methyl, ethyl, n-propyl, isopropyl, n-butyl, isobutyl, sec-butyl, tert-butyl, hydroxymethyl, and cycloalkyl.

16. The compound of claim 14, wherein at least one of $R_1$ and $R_2$ comprises a nitrogen salt and a counter ion, $X^-$, wherein $X^-$ is selected from the group consisting of $F^-$, $Cl^-$, $Br^-$, $I^-$, $CH_3SO_3^-$, and $R_{12}COO^-$, wherein $R_{12}$ is selected from the group consisting of hydrogen, an optionally substituted $C_1$ to $C_4$ alkyl group, an optionally substituted $C_2$ to $C_4$ alkenyl group, an optionally substituted $C_2$ to $C_4$ alkynyl group, an optionally substituted $C_1$ to $C_4$ alkyl group substituted with at least one halogen, an optionally substituted $C_1$ to $C_4$ alkyl group substituted with at least one hydroxyl group, an optionally substituted $C_3$ to $C_8$ cycloalkyl group, an optionally substituted $C_6$ to $C_{10}$ aryl group, and an optionally substituted $C_7$ to $C_{16}$ aralkyl group.

17. A lyotropic liquid crystal system comprising at least one lyotropic chromophoric compound of claim 1.

18. The lyotropic liquid crystal system of claim 17, wherein the lyotropic liquid crystal system is water-based.

19. The lyotropic liquid crystal system of claim 17, wherein the lyotropic liquid crystal system comprises a mixture of water and an organic solvent miscible with water.

20. The lyotropic liquid crystal system of claim 17, wherein the concentration of the lyotropic chromophoric compound in the lyotropic liquid crystal system is in the range of about 5% to about 50% by weight of the lyotropic liquid crystal system.

21. The lyotropic liquid crystal system of claim 17, further comprising one or more surfactants in an amount of up to about 5% by weight of the lyotropic liquid crystal system.

22. The lyotropic liquid crystal system of claim 17, further comprising one or more plasticizers in an amount of up to about 5% by weight of the lyotropic liquid crystal system.

23. The lyotropic liquid crystal system of claim 17, comprising a combination of two or more lyotropic chromophoric compounds of the formulae (I) and/or (II), wherein the amount of compound according to formula (I) is in the range of about 0% to about 99% by weight, based on the total amount of chromophoric compounds, and the amount of compound according to formula (II) is in the range of about 0% to about 99% by weight, based on the total amount of chromophoric compounds, provided that the total amount of compounds according to formulae (I) and/or (II) accounts for at least 50% of the total weight of all the chromophoric compounds in the lyotropic liquid crystal system.

24. The lyotropic liquid crystal system of claim 17, comprising a combination of two or more lyotropic chromophoric compounds of the formulae (VI) and/or (VII), wherein the amount of compound according to formula (VI) is in the range of about 0% to about 99% by weight, based on the total amount of chromophoric compounds, and the amount of compound according to formula (VII) is in the range of about 0% to about 99% by weight, based on the total amount of chromophoric compounds, provided that the total amount of compounds according to formulae (VI) and/or (VII) accounts for at least 50% of the total weight of all the chromophoric compounds in the lyotropic liquid crystal system.

25. The lyotropic liquid crystal system of claim 17, further comprising:
a first compound represented by the general formula (I) or (II), wherein at least one of $R_1$ and $R_2$ in the general formula (I) or (II) are each independently represented by the general formula (III), wherein the first compound has a concentration in the range of about 5% to about 50% by weight of the lyotropic liquid crystal system;

a second compound represented by the general formula (I) or (II), wherein at least one of $R_1$ and $R_2$ in the general formula (I) or (II) are each independently represented by the general formula (IV), wherein the second compound has a concentration in the range of about 5% to about 50% by weight of the lyotropic liquid crystal system; and a third compound represented by the general formula (I) or (II), wherein at least one of $R_1$ and $R_2$ in the general formula (I) or (II) are each independently represented by the general formula (V), wherein the third compound has a concentration in the range of about 5% to about 50% by weight of the lyotropic liquid crystal system.

26. The lyotropic liquid crystal system of claim 17, further comprising at least one water-soluble organic dye or an organic compound, the organic dye or organic compound being configured to participate in the formation of a liquid crystal.

27. An optically anisotropic film comprising at least one lyotropic chromophoric compound of claim 1.

28. The optically anisotropic film of claim 27, wherein the film is formed by depositing a lyotropic liquid crystal system comprising at least one lyotropic chromophoric compound onto a substrate.

29. The optically anisotropic film of claim 27, wherein the film is at least partially crystalline.

30. The optically anisotropic film of claim 27, further comprising at least one water soluble organic dye.

31. The optically anisotropic film of claim 27, wherein the film is a polarizing film.

32. The optically anisotropic film of claim 27, wherein the film is a phase-retarding film.

33. A liquid crystal display comprising at least one E-type polarizer, wherein the at least one E-type polarizer comprises a substrate and at least one optically anisotropic film of claim 27.

34. A method of forming an optically anisotropic film, comprising:
    applying a lyotropic liquid crystal system comprising at least one compound of claim 1 onto a substrate, wherein the lyotropic liquid crystal system comprises a plurality of liquid crystal mesophases; and
    orienting the plurality of liquid crystal mesophases.

35. The method of claim 34, wherein orienting the plurality of liquid crystal mesophases comprises spreading the lyotropic liquid crystal system in one direction.

36. The method of claim 34, further comprising drying said lyotropic liquid crystal system on the substrate.

37. The method of claim 34, further comprising forming the lyotropic liquid crystal system by mixing at least one compound selected from the general structural formulae (I) and (II) in water or a mixture of water and an organic solvent.

* * * * *